US006287848B1

(12) United States Patent
Hamzeh et al.

(10) Patent No.: US 6,287,848 B1
(45) Date of Patent: Sep. 11, 2001

(54) DOSAGE MODELING SYSTEM

(75) Inventors: Fayez M. Hamzeh; Paul S. Lietman, both of Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/370,910

(22) Filed: Aug. 10, 1999

Related U.S. Application Data

(62) Division of application No. 08/730,696, filed on Oct. 11, 1996, now Pat. No. 5,962,317.
(60) Provisional application No. 60/015,886, filed on Apr. 22, 1996, and provisional application No. 60/005,573, filed on Oct. 18, 1995.

(51) Int. Cl.[7] .................................................. C12M 1/36
(52) U.S. Cl. .................................. 435/286.7; 435/289.1; 435/297.5
(58) Field of Search .......................... 435/286.7, 289.1, 435/297.5

(56) References Cited

U.S. PATENT DOCUMENTS

| 3,883,393 | 5/1975 | Knazek et al. ........................ 195/1.8 |
| 4,559,299 | 12/1985 | Rotman .................................. 435/29 |
| 4,647,539 | 3/1987 | Bach ..................................... 435/284 |
| 4,937,187 | 6/1990 | Rotman ................................... 435/30 |
| 5,100,780 | 3/1992 | Haslbeck et al. ...................... 435/32 |
| 5,242,806 | 9/1993 | Yen-Maguire et al. ................ 435/32 |
| 5,278,048 | 1/1994 | Parce et al. ............................ 436/29 |
| 5,424,209 | 6/1995 | Kearney . |
| 5,962,317 | 10/1999 | Hamzeh et al. ....................... 435/325 |

FOREIGN PATENT DOCUMENTS

| 4 229 013 | 3/1994 | (DE) . |
| 0 632 131 | 1/1995 | (EP) . |
| 0 200 226 | 11/1996 | (EP) . |
| 9 105 253 | 4/1991 | (WO) . |
| 9 401 750 | 1/1994 | (WO) . |
| 9 428 501 | 12/1994 | (WO) . |

OTHER PUBLICATIONS

Blaser, J., et al., "Two Compartment Kinetic Model . . . ", Journal of Antimicrobial Chemo., vol. 15, 1985, Suppl. A., p. 131–137.
Moore et al., "A Single Large Dose of HPMPC . . . ", Program & Abstracts of the 6th Int'l Conf. On Antiviral Research, 04/93, p. 54.
Bilello, J., et al., "Effect of 2', 3' Didehydro–3'Deoxythymidine . . . ", Antimcrobial Agents & Chemo., Jun. 1994, 38(6) p. 1386–1391.
Reiken, S.R., et al., "The use if an Enzyme Single Fiber Reactor in the . . . ", Leukemia Research, vol. 17, No. 2, 1993, p. 121–128.
Blaser, J., et al., "Efficacy of Intermittent Versus . . . ", Anti–microbial Agents & Chemo., vol. 27, No. 3, Mar. 1985, p. 343–349.
Kurkela, R., et al., "Pilot–Scale Production of Murine Monoclonal Antibodies . . . ", BioTechiques, vol. 15, No. 4, 1993, p. 674–683.
Makino, M. et al., "Concentration of Live Retrovirus with A Regenerated . . . ", Archives of Virology, vol. 139, 1994, p. 87–96.
Tzianabos, A. O. et al., "Use of Hollow–Fiber Bioreactor for Production . . . ", Genetic Engineering News, vol. 24, Jan. 1995.
White, C.A., et al., "In Vitro Evaluation of the Determinants . . . " Antimicrobial Agents & Chemo., vol. 33, No. 7, 1989, p. 1046–1051.

(List continued on next page.)

*Primary Examiner*—David A. Redding
(74) *Attorney, Agent, or Firm*—Leydig, Voit & Mayer, Ltd.

(57) ABSTRACT

A monitoring system such as a drug dosage modeling system is disclosed. In preferred embodiments, the system provides mixing without the need for mechanical stirring.

8 Claims, 11 Drawing Sheets

OTHER PUBLICATIONS

Takeshita et al., "High Cell–Density Culture System of Hepato–Cytes . . . ", Artifical Organs, vol. 19, No. 2, 1995, pp. 191–193.

Moore et al., "Activity of (S)–1–(3–Hydroxy–2–Phosphonyl . . . ", Antimicrobial Agents & Chemo., vol. 38, No. 10, Oct. 1994, pp. 2404–2408.

Hamzeh, F. M., "Rational Approach to Dosing Antiviral Agents: The Development . . . ", Int'l Antiviral News, vol. 2, No. 9, Oct. 1994, p. 130–132.

Hamzeh, F. M. et al., "A Pharmacokinetic/Pharmacodynamic Approach . . . ", $8^{th}$ Int'l Conf. On Antiviral Research, Apr. 23–28, 1995.

DOSAGE MODELING SYSTEM

This is a divisional of application now U.S. Pat. No. 5,962,317 Ser. No. 08/730,696, filed on Oct. 11, 1996, the disclosure of which is incorporated by reference.

This application claims the benefit of U.S. Provisional Application Serial No. 60/005,573, filed Oct. 18, 1995, and U.S. Provisional Application Serial No. 60/015,886, filed Apr. 22, 1996, which are each incorporated by reference in their entireties.

TECHNICAL FIELD

The present invention describes a monitoring system, more particularly, a dosage modeling system which delivers therapeutic agents (e.g., drugs) to cultured cells in a bioreactor to simulate human pharmacokinetics and pharmacodynamics.

BACKGROUND OF THE INVENTION

Measuring the effect of drug dosage on living tissues is a very difficult and exacting science. Years of research and study may underlie determination of the proper dosage of a drug that will be prescribed to a patient. Drug characteristics are often accumulated using living hosts, such as animals.

The cost inefficiency and limitations of animal models have become pronounced in recent years. For example, it is expensive and time consuming to carry out studies with animals to provide clinical data. Moreover, in some situations, there may be no correlation between the animal model and the effect on a human, or there may be no suitable animal model. For example, certain human viruses are species specific and may have little or no effect on animals at all. The ethics of animal testing has also come into serious question.

The limitations of animal testing have popularized in-vitro studies, wherein dosing of a drug can be tested in an artificial system. For example, an antiviral drug can be tested by culturing or simply placing virus-infected cells into an artificial system which simulates human body characteristics. The cells in the artificial system are exposed to a concentration of the drug throughout the experiment. The artificial system can be used to measure, for example, the drug half-life, i.e., the time required to eliminate half of the quantity of drug that was present in the system relative to the point when the measurement began. The system can also be used to measure other aspects, such as the effectiveness of the drug at various concentrations, and the effect of drug dosing.

These studies are advantageous, as they provide preclinical data, which can be evaluated before investing the time and expense needed to provide clinical data. For example, the in-vitro studies can allow a researcher or drug manufacturer to more quickly and economically test a variety of approaches and dosages than would be possible with animal models. As a result, some of the more ineffective drugs and/or approaches can be avoided before clinical studies begin, which can provide a significant savings in both cost and time to the researcher and drug manufacturer.

However, the inventors of the present invention have noticed significant problems in these in-vitro techniques, and have recognized that there is no in-vitro model which is sufficiently representative of the in vivo (living) situation.

For example, one problem with the typical in-vitro system is that it continually exposes the pathogen-infected cells to a fixed concentration of the drug. The infected cells and cellular or viral proteins and nucleic acids are then continuously exposed to constant levels of both the drug and its intracellular metabolites. This dosing model is misrepresentative of the drug dosing that would actually occur in any living system. For example, in a living system, actual drug dosing follows a complicated curve that represents body factors such as absorption rate, the mechanics of how a drug is delivered to a cell, and clearance of the drug.

Additionally, a living system is frequently exposed to two or more drugs, and these drugs may interact in the system. For example, the interaction can be synergistic, whereby doses may be lowered to achieve less side effects from both drugs. Antagonistic drug interactions may be harmful and even fatal. Typical drug dosing models fail to represent the interactions between drugs.

Conventional drug dosing models may inaccurately represent the administered dosage at a particular point in time due to, for example, inadequate mixing of drug and fluid. Additionally, since modeling systems typically administer the drug through tubing, the model may fail to take into account the amount of drug that remains in the end of the tube before the amount reaches sufficient critical mass to fall as a drop. Each drop of drug can be significant, especially when a small volume of drug, and/or a concentrated drug, is used. Alternatively, or additionally, some modeling systems, e.g., that lack check valves, can allow some amount of drug backflow, and thus can fail to accurately represent the administered dosage. Thus, the deficiencies of conventional drug dosing models have prevented drug concentration-over-time/effect relationships in humans from being accurately characterized.

In addition to the disadvantages set forth above, conventional modeling systems use a relatively high volume of fluid, e.g., 100 ml; a relatively low flow rate, e.g., about 1 to 5 ml/min, and the systems require mechanical mixing (magnetic stirrers) and oxygenating coils. As a result, the system is relatively large, which can be undesirable, particularly when space is at a premium. Furthermore, the system is subsequently placed in an incubator to control the temperature of the fluid in the system, so the use of a large incubator is required. Thus, it can be difficult to find sufficient space for the system, or it may be difficult to find a suitably large incubator.

The present invention provides for minimizing or eliminating at least some of the disadvantages of the prior art. For example, the present invention can be used to more accurately evaluate various therapeutic agents to determine an effective dose range and appropriate indications. Embodiments of the invention can be used to provide effective preclinical studies to enhance clinical success. These and other advantages of the present invention will be apparent from the description as set forth below.

SUMMARY OF THE INVENTION

According to the present invention, an in vitro cell perfuision system is described in which both the concentration of one or more therapeutic agents (e.g., drugs and/or drug candidates), and the rate of elimination of the agent(s) can be manipulated and monitored in order to mimic first order human pharmacokinetics. The model of-the present invention can be used to study pharmacokinetics and pharmacodynamics of therapeutic agents such as, but not limited to, antiviral agents, antimicrobial agents (e.g., antibiotics), antineoplastic agents, antiarrhythmic drugs, cardiovascular drugs (e.g., antihypertensive drugs), antiinflammatory agents, immunosuppressive agents, immunostimulatory drugs, drugs used in the test of hyperlipoproteinemias, and asthma, drugs acting on the central nervous system (CNS), hormones, hormone antagonists, vitamins, hematopoietic agents, anticoagulants, thrombolytic and antiplatelet drugs. The model can also be used in toxicity studies, including toxicity studies involving metals, metal antagonists, and non-metal toxicants.

The relationship between the dose of a drug given to a patient and the utility of that drug in treating the patient's disease is described by two fundamental areas of pharmacology-pharmacokinetics (PK) and pharmacodynamics (PD). Pharmacokinetics concerns the absorption, distribution, biotransformation (metabolism, if it exists), and the elimination of drugs, i.e., what the body does to the drug. Relevant pharmacokinetic terms include $C_{max}$, the peak (maximum) concentration; AUC, the area under the drug concentration-time curve; $T_{max}$, the time of peak drug concentration; Cl (clearance rate), the measure of the body's ability to eliminate the drug (volume per unit time); volume of distribution, the ratio of the amount of drug in the body to the concentration of the drug in the blood; and $C_{min}$, the concentration before the next dose is administered.

Pharmacodynamics is the study of the relationship between drug concentration and intensity of pharmacological effect, i.e., what the drug does to the body. Relevant pharmacodynamic terms include $E_{max}$, the maximum effect, $ED_{50}$, the dose which produces 50% of the maximum effect, and $EC_{50}$, the concentration observed at half the maximal effect.

In accordance with the present invention, a system can be used to simulate the kinetics of therapeutic agents such as drugs and/or drug candidates. This system allows changing the pharmacokinetic parameters of the drug and/or drug candidate by changing the dosing characteristics. Embodiments of the present invention provide a PK/PD (pharmacokinetic/pharmacodynamic) system which mimics first order human pharmacokinetics, and defines a dose/response relationship when single or multiple doses are administered. Embodiments of the invention provide an effective PK/PD in vitro perfusion system. Agents of proven efficacy in man can be useful to compare the effectiveness of experimental therapies. For example, antiviral agents such as acyclovir, penciclovir, AZT, and interferons are useful for comparison studies.

The system according to the present invention allows simulation of various dosage techniques, including parenteral dosing, such as subcutaneous, intramuscular, and intravenous (continuous infusion) or oral administrations. Specific parameters involving absorption, distribution, and elimination can be simulated and manipulated for one or more drugs and/or drug candidates according to the present system.

Another advantage of the present invention is to simulate the rate with which the drug or drug candidate is being cleared or eliminated from the system. Thus, the invention can be used to simulate drug half-life ($t_{1/2}$). The invention can also be used to measure and evaluate other drug dosing parameters such as drug concentration, as well as exposure as measured by the area under the drug concentration-time curve (AUC).

The present invention provides for monitoring the relationship of the extracellular concentration of a drug and/or drug candidate to the intracellular concentration of a drug and its metabolites, e.g., metabolites such as phosphorylated metabolites. This is especially desirable since the intracellular metabolites in humans cannot be measured. Thus, the present invention allows one to model the relationship between the concentrations of metabolites of a drug, and the drug's efficiency and toxicity. Embodiments of the present invention provide for monitoring intracellular, extracellular, and/or membrane-associated metabolites of drugs and/or drug candidates.

In addition to being able to measure and analyze extracellular and intracellular concentration of at least one therapeutic agent and its metabolites, the system allows one to measure, in a time-dependent fashion, the effect of these parameters on pathogen and cellular products, e.g., DNA, RNA (mRNA), and other products. In this system, one has access to the target cells where the agent will produce its effect, so one can measure pathogen and cellular DNA, RNA, and proteins, such as core proteins, receptors, antigens (e.g., autoantigens, alloantigens, heteroantigens), antibodies, and enzymes. In particular, HIV encodes for enzymes such as reverse transcriptase, and integrase. HIV viral genes and their gene products such as env (gp160, gp120, gp41); pol (p66, p51, p31); gag (p55, p24, p17), tat (p14), and rev (p20), can be measured and monitored. Inhibition of the production of critical genes and viral proteins by new drugs is desired to prevent the formation of, for example, mature core proteins and virions. Other examples include the measurement of antigens such as autoimmune and tumor associated antigens. Autoantigens are associated with diseases (autoimmune thyroiditis, myasthenia gravis, arthritis, lupus). Cell surface tumor associated antigens (TAA) have been associated with RNA and DNA viruses. Viral antigens have been associated with the following cancer types: nasopharyngeal carcinoma (EBV), cervical carcinoma (human papilloma virus), hepatocellular carcinoma (hepatitis B virus), T cell leukemia and lymphomas (human T-lymphotropic virus). Normal cellular antigens may also be tested.

For example, measuring prostate-specific antigen (PSA) levels in prostatic cancer and CA 125 levels in patients with ovarian cancer may be valuable as new drugs are tested.

Embodiments of the present invention provide access to the site of action of the therapeutic agent (e.g., an antiviral drug), while the extracellular concentration is changing in a time-dependent fashion simulating human pharmacokinetics, allowing investigation of the relationship between the extracellular concentration and the intracellular concentration of the drugs and their metabolites, especially the phosphorylated metabolites. Intracellular pharmacokinetic and pharmacodynamic parameters of, for example, nucleoside analogues and their phosphates, as a function of changing extracellular drug concentration may provide a better indicator of antiviral activity than extracellular pharmacokinetic parameters. The present invention is especially desirable since intracellular half-life ($t_{1/2}$) of the active metabolite of different drugs may vary.

In some embodiments, the present invention provides for studying the relationship between extracellular area under the drug concentration-time curve (AUC) and intracellular AUC by measuring the intracellular triphosphates of several nucleoside analogues. The intracellular AUC, where "C" is the intracellular concentration of the triphosphates, can provide a more accurate measure of drug exposure than extracellular AUC. In an embodiment, the present invention provides for studying the correlation between intracellular levels of therapeutic agents and their metabolites such as, for example, an antiviral agent such as AZT and its metabolites, and efficacy and/or toxicity.

Embodiments of the system according to the present invention can be used to simulate and monitor the interactions between two or more drugs, and to define a dose/response relationship when multiple drugs are administered. Since drugs may interact antagonistically, or synergistically, doses of each drug can be changed to determine an optimum result, and reduce or eliminate drug-related toxicities. Optimization of multiple drug therapies is critical because combination therapy is more commonplace among HIV-infected individuals and cancer patients. Standard antiviral therapy for HIV infection involves three drugs (AZT, 3TC, and a protease inhibitor) or more.

Another advantage of the present invention is to minimize the size of the system, e.g., by minimizing the number of parts or components, and/or by reducing their size. For example, embodiments of the invention facilitate mixing and gas exchange while avoiding the need for a stirring element (e.g., a magnetic stirrer) in the central reservoir, and while avoiding the need for oxygenating coils. Alternatively, or additionally, embodiments of the invention can be carried out without a central reservoir.

Additionally, since the simulation can be carried out using a reduced volume of fluid, the size of some of the components in the system can be reduced. Thus, a dosage simulation system having two or more units, preferably two or more units operating in parallel, can be placed in a relatively small area. For example, in one embodiment, the system according to the invention can be a desktop system. Since the therapeutic agent(s) can be expensive and/or available in limited quantities, another advantage of reduced size is that a less of the agent(s) may be needed for testing.

Yet another advantage of the present invention is to provide an automated or semi-automated monitoring system.

Embodiments of the present invention also provide a connectorized system for a plurality of connected objects. For example, this allows one to avoid confusion between tubes and correctly connect a number of dosing systems in parallel.

SPECIFIC DESCRIPTION OF THE INVENTION

Figure 1:
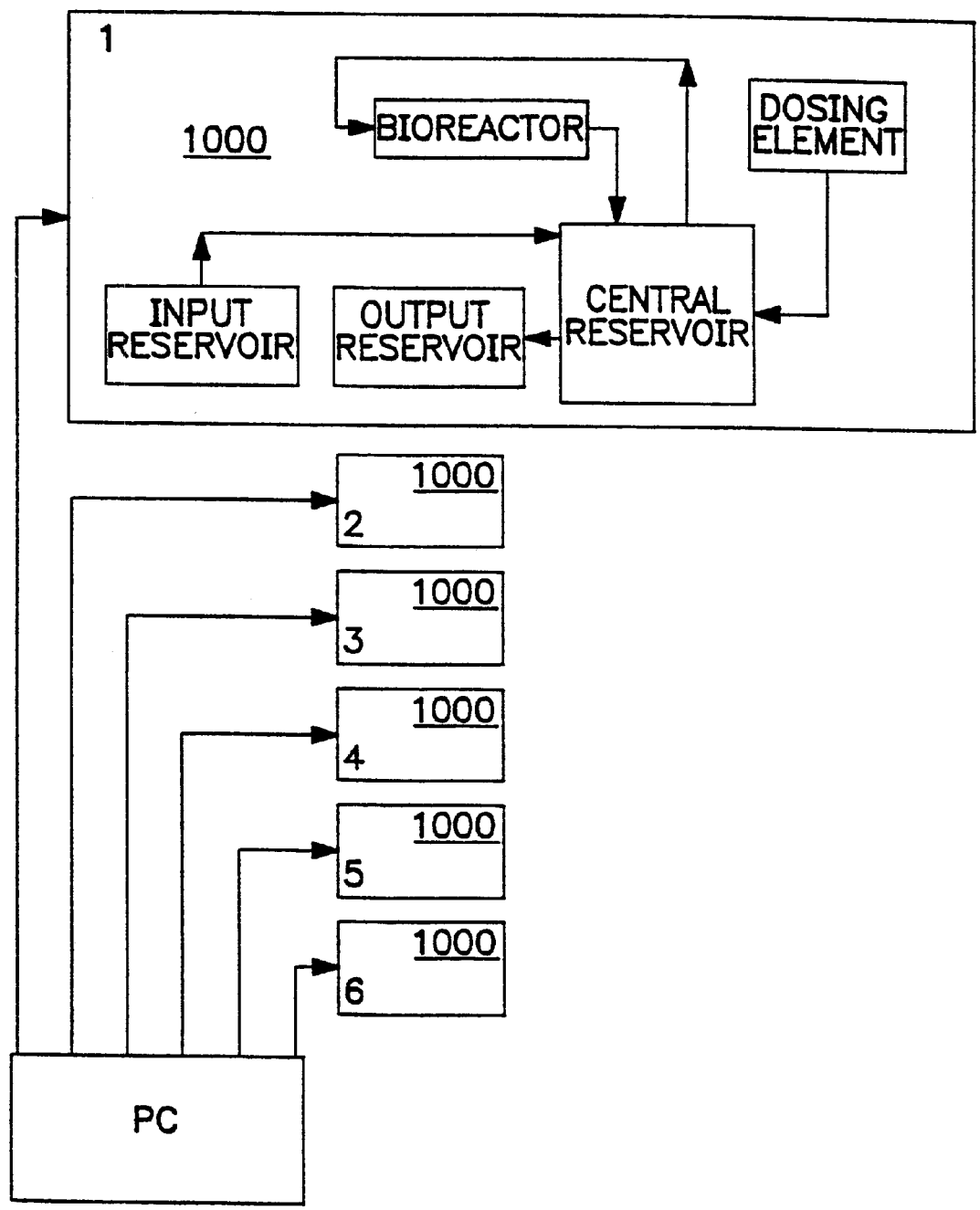
FIG. 1 shows a block diagram of an embodiment of a system according to the present invention, wherein 6 dosing systems are operating in parallel.

In accordance with illustrative embodiments of the invention, a method of monitoring comprises circulating a simulated body fluid along a first circulation loop in fluid communication with a bioreactor including cells and a dosing element capable of passing at least one therapeutic agent into the first circulation loop; passing the therapeutic agent into the first circulation loop and mixing the therapeutic agent with said simulated body fluid; removing a mixture of therapeutic agent and simulated body fluid from the first circulation loop; and monitoring the effect of the therapeutic agent on the cells in the bioreactor. In an embodiment, the method includes passing diluent fluid into the first circulation loop and mixing the diluent fluid with the therapeutic agent and the simulated body fluid; removing a mixture of diluent fluid, therapeutic agent, and simulated body fluid from the first circulation loop; and monitoring the effect of the therapeutic agent on the cells in the bioreactor. Typically, the method provides for the dosing of at least one drug. Some embodiments provide for the dosing of at least two drugs.

In accordance with an embodiment of the invention, a method of monitoring comprises circulating a simulated body fluid along a first circulation loop in fluid communication with a central reservoir and a bioreactor including cells; mixing at least one therapeutic agent with the simulated body fluid, wherein mixing the therapeutic agent with the simulated body fluid includes passing the therapeutic agent and the body fluid through a mixing arrangement into the central reservoir, the mixing arrangement including a first therapeutic agent port and a simulated body fluid port cooperatively arranged to allow the simulated body fluid to wash the therapeutic agent from the therapeutic agent port; and monitoring the effect of the therapeutic agent on the cells in the bioreactor. Typically, the method provides for modeling the dosing of at least one drug, and includes passing a diluent fluid through a diluent port in the mixing arrangement, and washing the diluent fluid and the drug from the diluent fluid and drug ports with the simulated fluid. In an embodiment, the method includes measuring the concentration of at least one metabolite of a drug, preferably the intracellular concentration of at least one metabolite of a drug. Some embodiments include measuring the intracellular concentration of at least two metabolites of a drug. Other embodiments provide for measuring the concentration of a plurality of metabolites of a plurality of drugs.

In some embodiments, the method can also provide for modeling the absorption to simulate oral administration of the therapeutic agent.

Embodiments of the invention provide a modelling system comprising a bioreactor including cells in fluid communication with a mixing arrangement including at least three ports, the first port being positioned near the second port and the third port. In an embodiment, the system also includes a central reservoir.

In an embodiment, a modelling system comprises a bioreactor loop including a bioreactor having cells contained therein, and a dosing element in fluid communication with the bioreactor loop.

Embodiments of the invention provide a device comprising a reservoir; a mixing arrangement that is coupled to the reservoir; the mixing arrangement including a bioreactor loop port, a diluent loop port, and a therapeutic agent port; and the bioreactor loop port being positioned near the diluent loop port and the therapeutic agent port.

Embodiments of the invention provide a device comprising a reservoir; a mixing arrangement that is coupled to the reservoir; the mixing arrangement including at least three ports, the first port being positioned near the second port and the third port.

In accordance with illustrative embodiments of the invention, a monitoring system is provided comprising a first reservoir; a mixing arrangement that is coupled to the reservoir; the mixing arrangement including a bioreactor loop conduit including a bioreactor loop port, a diluent loop conduit including a diluent loop port, and a therapeutic agent conduit including a therapeutic agent port; the bioreactor loop port being positioned near the diluent loop port and the therapeutic agent port; wherein the diluent loop conduit, the therapeutic agent conduit, and the bioreactor loop conduit each extend into the reservoir. In an embodiment, the diluent loop conduit and the therapeutic agent conduit each extend axially into the reservoir. Preferably, the system provides for modeling the dosing of at least one drug. In some embodiments, the system includes additional reservoirs. In an embodiment, the system includes an additional reservoir and an additional mixing arrangement, wherein the additional mixing arrangement has at least three ports and is coupled to the additional reservoir.

In accordance with some embodiments of the invention, the system includes a central reservoir and a mixing arrangement including a bioreactor loop conduit including a bioreactor loop port, a diluent loop conduit including a diluent loop port, and a therapeutic agent conduit including a therapeutic agent port. In other embodiments, the system lacks a central reservoir and/or lacks such a mixing arrangement.

Figure 2:
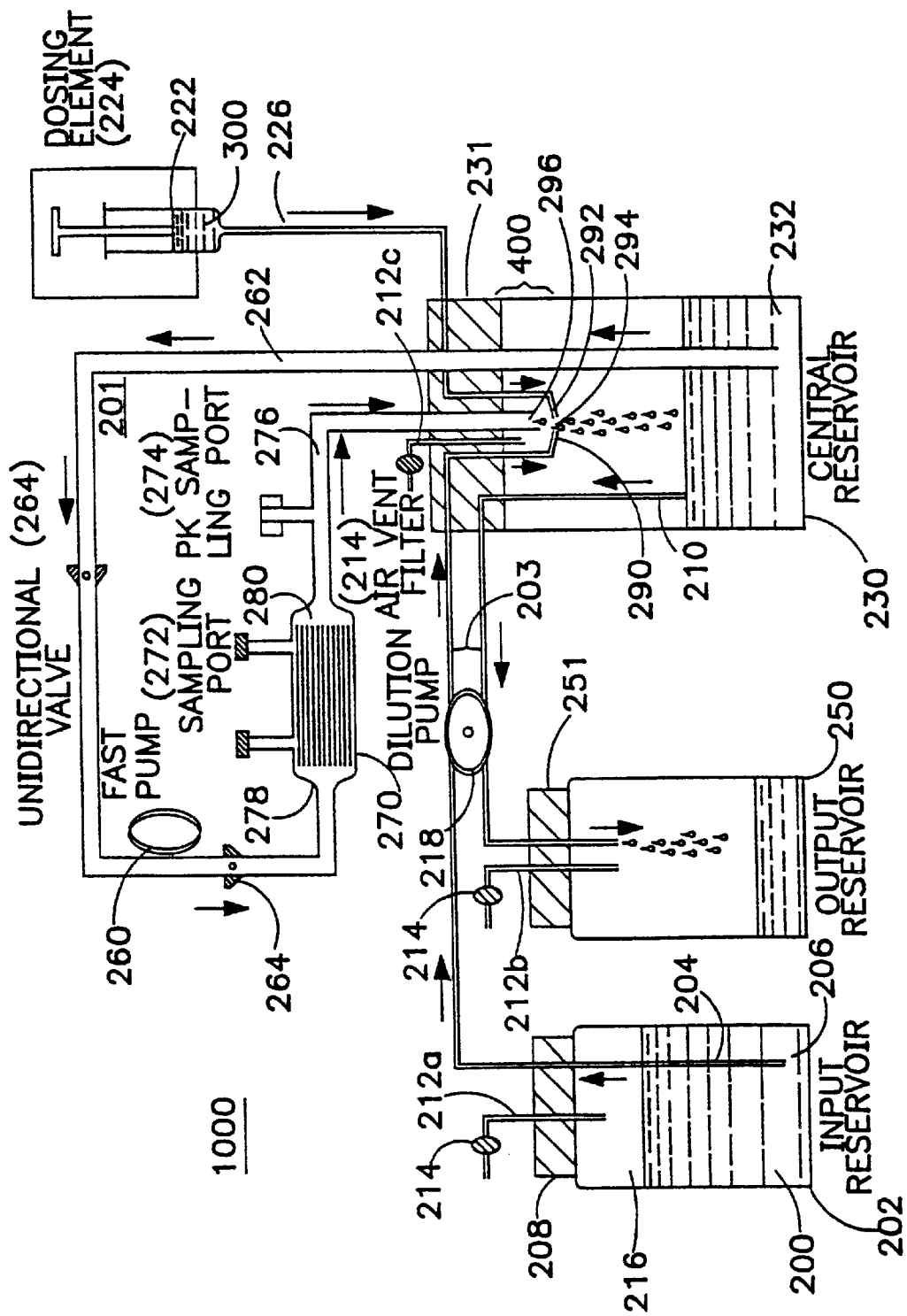
FIG. 2 shows one embodiment of a single dosing system of the present invention.

An embodiment including a plurality of dosing systems operating in parallel is shown in FIG. 1, and FIG. 2 illustrates an embodiment of a single dosing system 1000. In the illustrated embodiments, like components have like reference numbers. The basic system of the present invention models the human or animal circulatory system, and circulates a fluid that represents the internal fluids of the body, through the bioreactor that simulates a human or animal tissue system.

Each dosing system 1000 includes a bioreactor 270 containing the material to be exposed to at least one fluid 232 that, typically, will also contain the therapeutic agent(s) 300. The system circulates the fluid 232, that represents the internal fluids of the body, through the bioreactor 270. Preferably, the bioreactor, which mimics the characteristics of the human or animal tissue system, contains cultured bacterial or mammalian cells. In one preferred embodiment, the cultured cells are infected with a pathogen, e.g., with a virus or bacterium. As will be noted in more detail below, the fluid 232 (sometimes referred to as the simulated body fluid), can be an actual body fluid such as plasma, or a synthetic fluid such as a cell culture medium. A fast pump 260, which operates to circulate fluid through the bioreactor 270, represents a human or animal heart.

Figure 9:
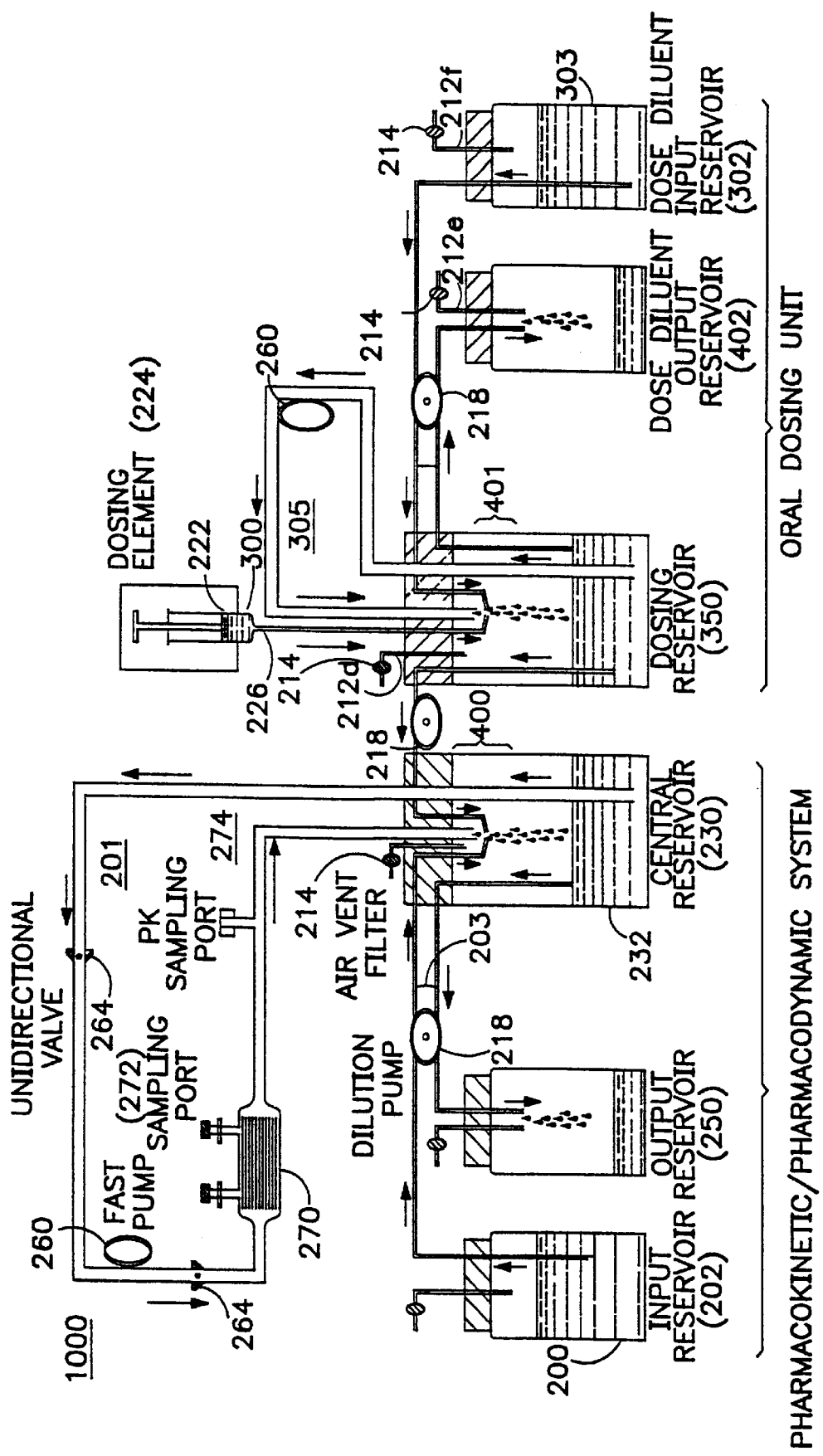
FIG. 9 shows an embodiment of a single dosing system representing oral absorption.
Figure 13:
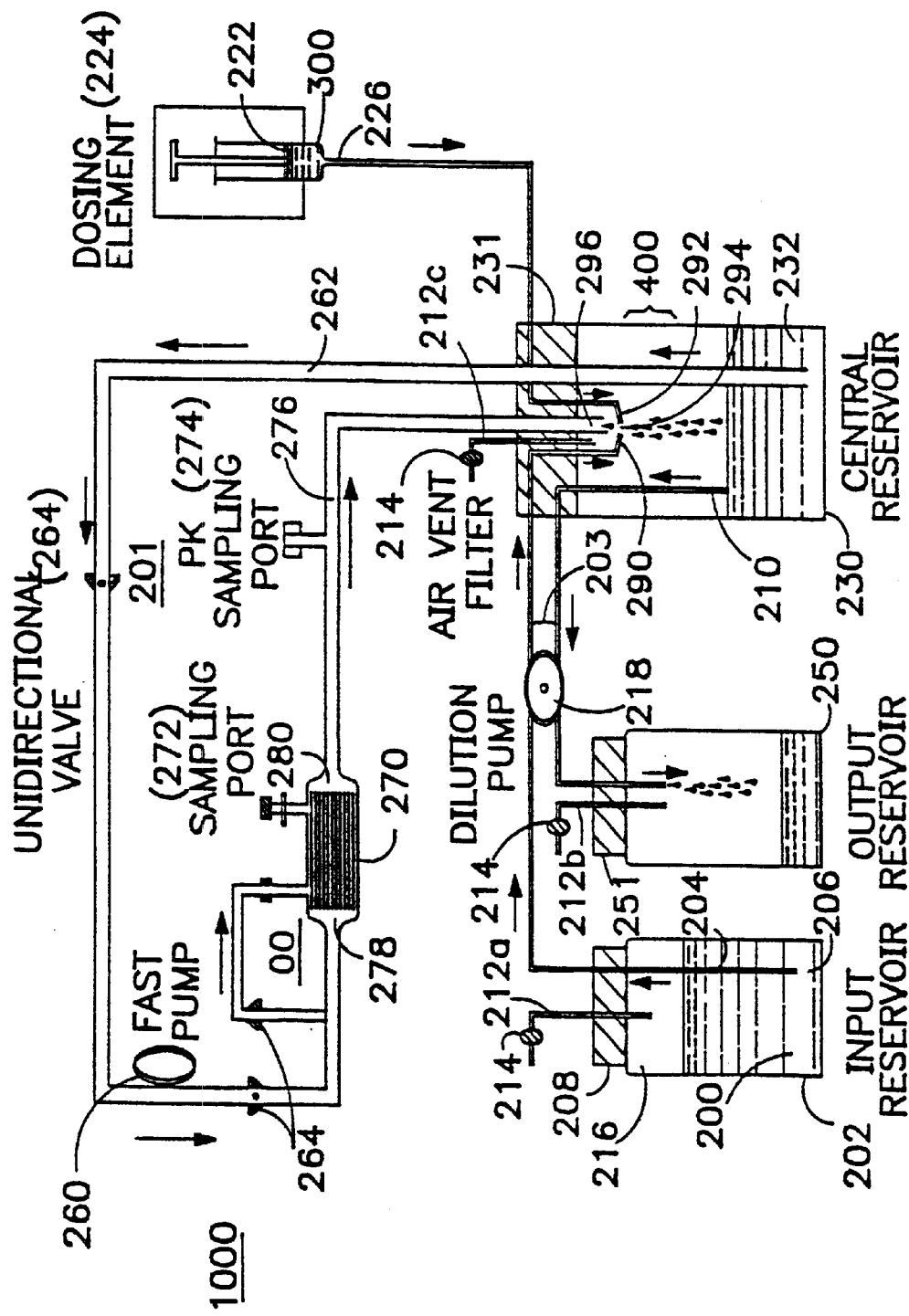
FIG. 13 shows an embodiment of a single dosing system including a shunt.
Figure 14:
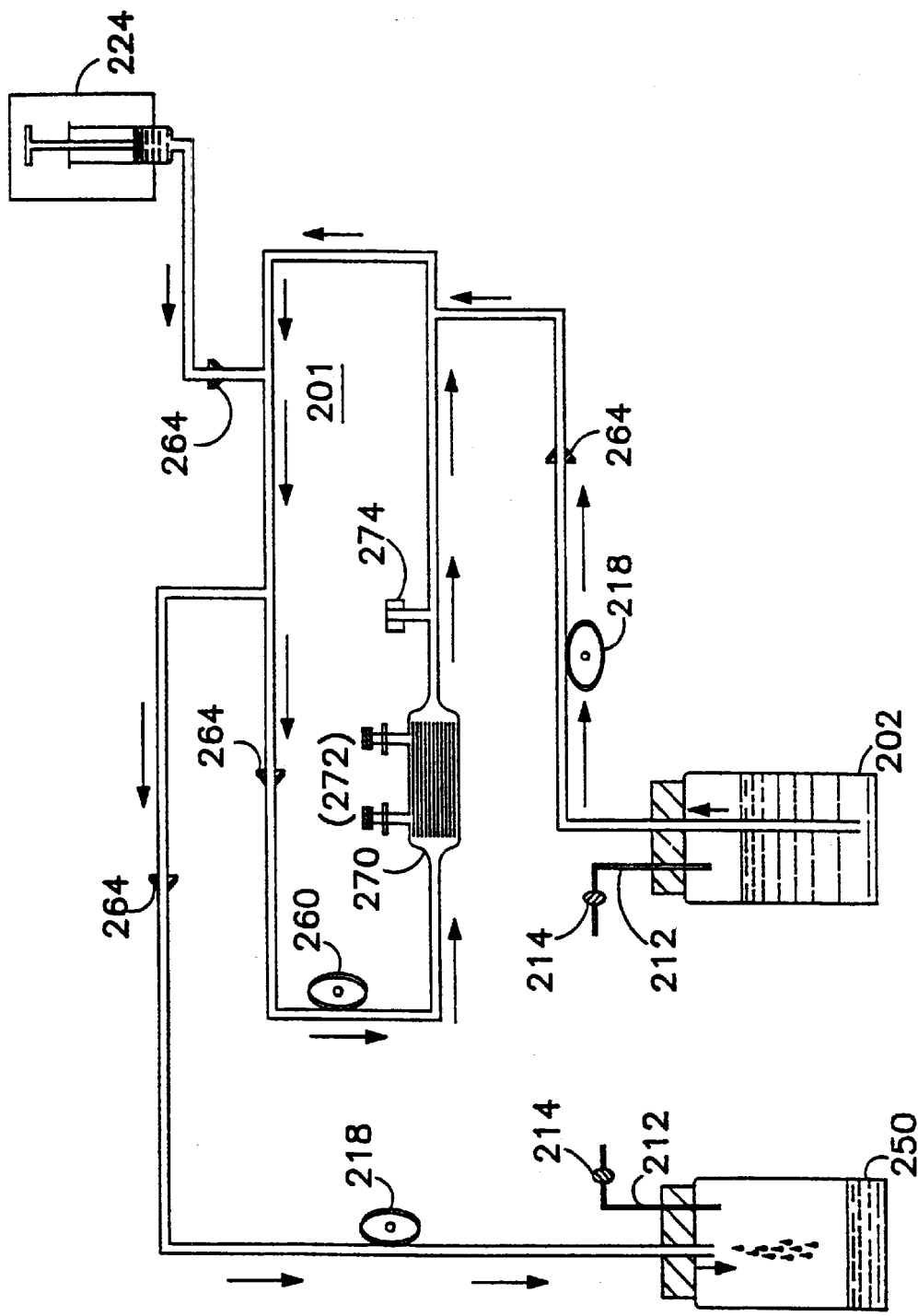
FIG. 14 shows another embodiment of a single dosing system that can be utilized without a central reservoir.

The embodiments illustrated in, for example, FIGS. 2, 9, and 14, show more detailed views of the single dosing system 1000, that circulates the fluid 232. Using FIG. 2 for reference, a dosing system 1000 includes a bioreactor 270, and a first circulation loop (or bioreactor loop) 201 for circulating fluid 232 from a central reservoir 230, through the bioreactor, and back to the reservoir 230. A pump 260 passes fluid 232 through the first circulation loop 201. Bioreactor 270 includes at least one port, e.g., sampling port 272, and typically includes two or more ports. The system 1000 illustrated in FIGS. 2, 9, and 12–14 includes an additional port, PK sampling port 274.

In those embodiments including a central reservoir, the dosing system 1000 allows the amount of fluid 232 in the bioreactor loop 201 and the central reservoir 230 to remain essentially constant while adding and removing fluid from central reservoir 230. Thus, the dosing system also includes a second circulation (or diluent loop) 203 that allows the amount of fluid added to the central reservoir 230 to be offset by the amount of fluid removed from the reservoir 230. Accordingly, in the embodiments illustrated in FIGS. 2, 9, 12, and 13, second circulation loop 203 allows diluent fluid 200 to be passed from input reservoir 202 into central reservoir 230, and allows fluid from the central reservoir 230 (i.e., the fluid 232 diluted with fluid 200) to be passed into output reservoir 250. A pump 218 passes fluid through the second circulation loop 203.

In those embodiments lacking a central reservoir, e.g., as illustrated in FIG. 14, the dosing system 1000 also allows the amount of fluid 232 in the bioreactor loop 201 to remain essentially constant, e.g., by adding fluid from the input reservoir 202 while removing fluid and passing it into the output reservoir 250. In the embodiment illustrated in FIG. 14, a plurality of pumps 218 can be used to add and remove fluid. In other embodiments, a single pump 218 can be used to add fluid to the loop 201 and remove fluid from the loop.

As will be noted in more detail below, pump 260 (associated with the first circulation loop 201) operates at a higher flow rate than pump 218 (associated with the second circulation loop 203, for example). In some embodiments, the system can include additional pumps. For example, the embodiment illustrated in FIG. 9 shows two pumps 260, and three pumps 218, and the embodiment illustrated in FIG. 14 shows two pumps 218.

Figure 12:
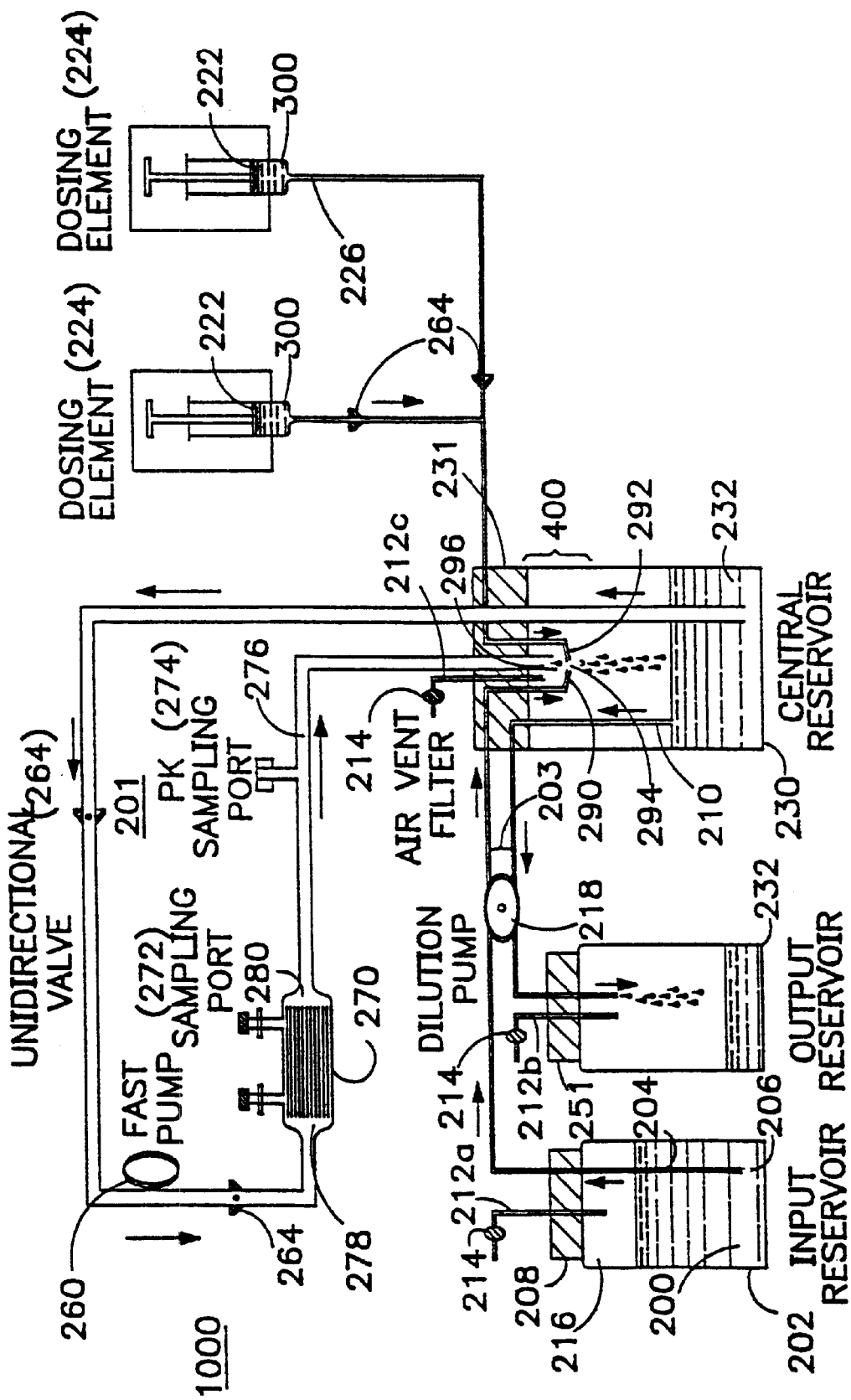
FIG. 12 shows an embodiment of a single dosing system providing for dosing with two therapeutic agents.

The system 1000 provides for exposing cells in the bioreactor 270 to the therapeutic agent(s) 300, i.e., by mixing the agent with the fluid 232 to be passed through the bioreactor 270. Accordingly, as illustrated in, for example, FIG. 2, the system 1000 includes dosing element 224, that, once a pressure differential is created, passes the therapeutic agent 300 (e.g., a drug) into the central reservoir 230. Alternatively, as illustrated in, for example, FIG. 14, the system 1000 includes dosing element 224, that, once a pressure differential is created, passes the therapeutic agent 300 (e.g., a drug) into the loop 201. The system can include a plurality of dosing elements. For example, as illustrated in FIG. 12, a plurality of dosing elements can be utilized, to pass a plurality of therapeutic agents into the central reservoir 230.

Fluid 232 in the reservoir 230 (that now typically includes the therapeutic agent 300) is subsequently passed through the bioreactor 270. With respect to the embodiment illustrated in FIG. 14, fluid 232, typically including the therapeutic agent 300, is subsequently passed through the bioreactor 270. In the embodiment illustrated in FIGS. 2 and 3, the central reservoir 230 has coupled thereto a mixing arrangement 400 that allows fluid passing from the bioreactor 270 to mix with the therapeutic agent 300 and the diluent fluid 200. Fluid 232, which is now a mixture of fluid passing from the bioreactor, diluent fluid, and therapeutic agent, is passed through the bioreactor 270. Alternatively, fluid passing from the bioreactor can be mixed with the therapeutic fluid and diluent fluid without using the mixing arrangement 400. For example, using the illustrative embodiment according to FIG. 14 for reference, fluid passing from the bioreactor can be mixed with the therapeutic fluid and diluent fluid without using the mixing arrangement 400, and therapeutic agent can be added at any desired location in the system, e.g., via a thin-bore needle.

Of course, in another embodiment similar to that illustrated in FIG. 14, e.g., a system lacking a central reservoir, the system may also include a mixing arrangement 400 that provides for mixing fluid passing from the bioreactor, diluent fluid, and therapeutic agent.

Embodiments of the invention provide for operation of a plurality of dosing systems, preferably operating in parallel, wherein at least one of the dosing systems is a control. For example, in one embodiment, eight dosing systems are operated in parallel, wherein two of the systems are controls. In some embodiments, a plurality of types of controls are utilized. For example, while at least one control in each embodiment will be free of the therapeutic agent to be tested, embodiments may include additional controls where the additional control is a different therapeutic agent. For example, the additional control can be an FDA approved drug, e.g., AZT, that is used for reference when testing a new drug for treating HIV. Thus, the dosing systems allow a comparison between the therapeutic agent to be tested, a therapeutic agent-free control, and an FDA approved drug control.

Preferred embodiments provide for parallel operation of at least four, and more preferably, at least six dosing systems 1000 (as illustrated in FIG. 1), with each dosing system including a separate bioreactor 270, bioreactor loop 201, and central reservoir 230. However, while a separate bioreactor, bioreactor loop, and central reservoir is utilized for each dosing system, the systems can be operated, preferably in parallel, utilizing a common input reservoir 202 and output reservoir 250 if desired. Thus, a single input reservoir 202 can contain a sufficient volume of diluent fluid 200 to supply a plurality of dosing systems, and a single output reservoir 250 can be sufficiently large to contain the fluid removed from the plurality of dosing systems.

Optionally, one or more additional reservoirs can be used, e.g., to model the site of absorption after oral administration if such is desired. For example, FIG. 9 illustrates a dosing reservoir 350, a dose diluent input reservoir 302 containing dose diluent fluid 303, a oral dose diluent loop 305, and a mixing arrangement 401 with a plurality of ports, and a dose diluent output reservoir 402. The mixing arrangement 401 coupled to the dosing reservoir 350 allows fluid passing from the oral dose diluent loop 305 to mix with a therapeutic agent 300 and a dose diluent fluid 303. The resultant fluid, that is a mixture of therapeutic agent 300, and dose diluent fluid 303, is transferred to the central reservoir 230. Dose diluent fluid 303 lacks therapeutic agent, and has essentially the same composition as diluent fluid 200. Thus, dose diluent fluid is an actual and/or synthetic body fluid.

In a variation of the embodiment of FIG. 9, a device such as an automated programmable pump can be used to eliminate components such as the dosing reservoir 350, the dose diluent input reservoir 302, the oral dose diluent loop 305, the mixing arrangement 401, and the dose diluent output reservoir 402. As a result, the size of a system for modelling oral dosing can be reduced.

Typically, as shown in FIGS. 2, 9, 12–14, the system includes one or more flow control devices 264, preferably unidirectional flow control devices such as check valve(s) to minimize or eliminate the possibility of backflow while the system is operating. A variety of flow control devices 264 are suitable for carrying out the invention. For example, flow control device 264 can be a clamp or valve, preferably operated by an automated system.

The system can also include one or more vents. For example, in the embodiment illustrated in FIG. 2, input reservoir 202, central reservoir 230, and output reservoir 250 are each associated with a separate pressure balancing tube 212 (212a, 212b, 212c) including an air vent with an air filter 214. FIG. 9 illustrates additional reservoirs and associated vents.

The system can include a variety of other components such as connectors, tubing, ports, and loops. For example, in the embodiment illustrated in FIG. 13, the system includes a shunt loop 500, communicating with an extra port of bioreactor 270.

Each of the components or elements of the invention will now be described in more detail below.

The bioreactor 270 is suitable for containing the material, e.g., cultured bacterial or mammalian cells, to be exposed to the therapeutic agent(s). If desired, the cells can be bioengineered and exposed to the therapeutic agent(s) in accordance with the invention, e.g., to monitor gene expression and/or gene therapy. The bioreactor as used herein preferably includes dosage simulating materials, and body simulating materials therein. The dosage simulating materials include, for example, cultured cells, or any other similar material which the therapeutic agent has an effect thereon.

A wide variety of pathogens are suitable for carrying out the invention. Preferably, the cultured cells are infected with a pathogen, e.g., a virus, bacterium, fungus (including molds and yeasts), or a protozoan. For example, in those embodiments wherein the pathogen is a virus, suitable viruses include DNA viruses, including, but not limited to HSV (herpes simplex virus), VZV (varicella-zoster virus), HCMV (human cytomegalovirus), and RNA viruses, including, but not limited to, Paramyxoviridae, Reoviridae, Picornaviridae, Rhabdoviridae, Flaviviridae, Retroviridae such as HIV (human immunodeficiency virus), and other viruses. In those embodiments wherein the pathogen is a bacterium, suitable bacteria include, but are not limited to, Cocci (e.g., *Neisseria spp.*, and *Streptococcus spp.*); Bacilli (e.g., *Escherichia coli, Mycobacterium spp., Clostridium spp., Salmonella tuphi,* and *Chlamydia spp.*); Spirilla, and Spirochetes. Suitable protozoans include, but are not limited to, Ciliates, Flagellates (including *Trypanosoma spp.*), and Sporozoa (including *Plasmodium spp.* and *Toxoplasma gondii*). Suitable fungi include, but are not limited to, those that cause Candidiasis, Histoplasmosis, and Ringworm.

The body simulating materials include structures which simulate, for example, capillaries and extra-cellular spaces, as described herein.

A variety of bioreactors are suitable for carrying out the invention. Typically, the bioreactor provides for physically retaining the cells, e.g., trapping or immobilizing them in or on the outside of hollow fibers, in ceramic matrixes or between planar membranes; or microencapsulating or immobilizing them in beads.

In a preferred embodiment, the bioreactor 270 includes a cartridge suitable for culturing the cells. Cartridges for carrying out the invention are commercially available, for example, from Unisyn Technologies, Inc. (Hopkinton, Mass.). The cartridge, which is preferably a fiber cartridge, is typically formed of multiple cellulose or polypropylene capillaries. The capillaries divide the cartridge into two compartments, an intra-capillary compartment and an extra-capillary compartment.

Figure 4:
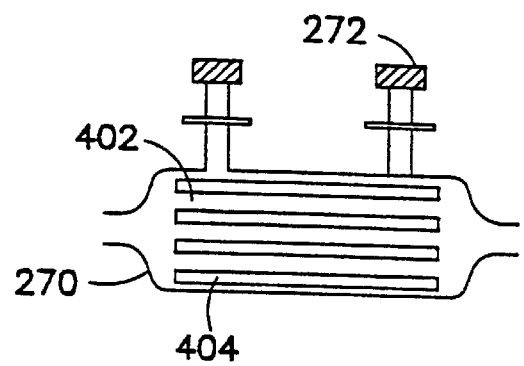
FIG. 4 shows a side view of a bioreactor cartridge.
Figure 5A:
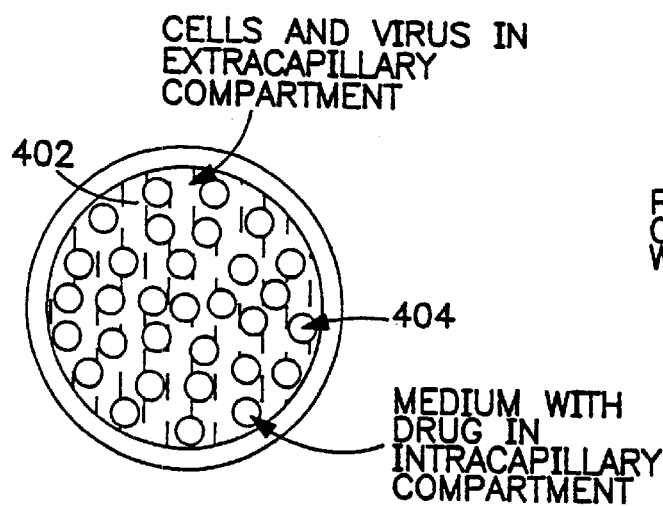
FIGS. 5A and 5B show close-up inside views of the bioreactor.
Figure 5B:
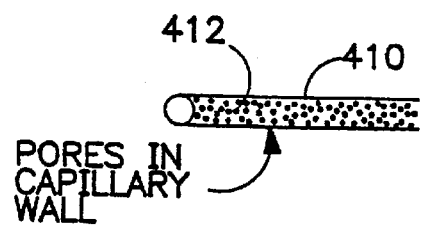

Embodiments of the bioreactor 270 are shown in detail in FIGS. 4, 5A and 5B. An intra-capillary compartment 404 is used to perfuse the cells. An extra-capillary compartment 402 plates the cells within the extra-cellular space, and, in some embodiments (e.g., as illustrated in FIG. 13 including shunt loop 500), is used during supplemental perfusion. The intra-capillary compartment and extra-capillary compartment are connected by micropores that allow selected molecules or materials to move between the two compartments. Molecules which have the proper sizing can move between compartments in this way. In the illustrated embodiments intra-capillary compartment 404 includes capillary walls 410 which are perforated 412 to allow the simulated body fluid to enter the extra-capillary compartment 402.

Using FIG. 13 for reference, the use of shunt loop 500 can provide rapid equilibrium between the intra-capillary and extra-capillary compartments, e.g., to carry out the dosing protocol more quickly and to increase the transfer of the therapeutic agent. The rate of achieving equilibrium can be varied by, for example, changing the ratio of the lumen of the shunt tubing to the lumen of the inlet of the bioreactor.

The drug concentration can be measured both in the intra-capillary space and the extra-capillary space to simulate the effects on different body elements. In some embodiments, e.g., wherein the cultured cells in the bioreactor 270 are infected with a virus or bacterium, samples from the intra-capillary compartment 404 and the extra-capillary compartment 402 are taken (e.g., through sampling port 272) for measuring the drug concentration, and for determining the viral or bacterial titer. The cells can be harvested from the extra-capillary compartment 402 at specified time points for determination of, for example, metabolites (particularly intracellular metabolites) and/or for the determination of intracellular viral DNA. One technique for measuring intracellular phosphates utilizes high pressure liquid chromatography (HPLC).

In those embodiments including a central reservoir, the intra-capillary compartment is in fluid communication with central reservoir 230. Using the embodiment illustrated in FIG. 2 for reference, central reservoir 230 contains a quantity of fluid 232 to represent the internal fluids of the body, more preferably the human body. Of course, the total amount of fluid in the central reservoir 230 is much less than that of the typical human body. Fluid 232 is a perfusion medium that delivers nutrients, oxygen and one or more therapeutic agent(s) 300 to the cells in the bioreactor 270. The fluid 232 can simulate one or several characteristics of body fluid.

The fluid 232 can be an actual body fluid such as, for example, plasma, and/or the fluid can be a synthetic body fluid, e.g., a culture medium such as Dulbecco's Modified Eagle Medium (DMEM), RPMI-1640, and a $CO_2$ independent medium. The fluid 232 can contain an actual or synthetic component of body fluid. In some embodiments, an actual body fluid, such as plasma, can be modified, e.g., diluted, before using it according to the invention. The fluid can contain a mixture of actual and synthetic fluids. Fluid 232 can include additional components or ingredients. For example, fluid 232 can also include materials useful for maintaining cultured cells, e.g., nutrients and/or buffers.

As will be noted in more detail below, at least one therapeutic agent 300 (e.g., a drug) and diluent fluid 200 will typically also be introduced into central reservoir 230 or first circulation loop 201 and mixed with fluid 232.

A first circulation loop (or bioreactor loop) 201 passes the simulated body fluid 232 (that eventually will contain the therapeutic agent 300 and diluent fluid 200) through the bioreactor 270 containing the cultured cells. The fluid in the intracellular compartment continuously exchanges nutrients, oxygen, and carbon dioxide, and therapeutic agent will pass into the extracapillary fluid. Flow allows components of the fluid to pass back and forth between the extra- and intra-capillary compartments and subsequently into the central reservoir through return tube 276.

The operation of first pump (also known as the fast pump) 260 circulates fluid 232 at a high flow rate through first circulation loop 201 from central reservoir 230, through tube 262 and bioreactor 270, and back into central reservoir 230. In those embodiments lacking a central reservoir 230 (e.g., as illustrated in FIG. 14), the first pump 260 circulates fluid 232 at a high flow rate through first circulation loop 201 bioreactor 270.

Typically, the flow rate of the first pump 260 is about 15 ml/min or more, and the total amount of fluid in the loop 201 and the central reservoir 230 is about 50 ml or less. However, in some embodiments, the total amount of fluid in the loop 201 and the central reservoir 230 can be greater than 50 ml, particularly if the flow rate of the first pump is about 20 ml/min or more. The total amount of fluid in the loop 201 and the central reservoir 230 is known as the Volume of Distribution (VD).

If desired, a single fast pump 260 (e.g., a peristaltic pump associated with a plurality of tubes) can be utilized with a plurality of dosing systems 1000, e.g., to circulate fluid along a plurality of bioreactor loops. A variety of such pumps are suitable for carrying out the invention and are known in the art.

Input reservoir 202 stores diluent fluid 200, that represents new body fluid, i.e., the internal fluid(s) of the body free of the therapeutic agent(s). Since diluent fluid 200 is new fluid free of the therapeutic agent, it has essentially the same composition as fluid 232 before fluid 232 was exposed to a therapeutic agent. Thus, diluent fluid 200 is an actual and/or synthetic body fluid as described with respect to fluid 232 above, and can contain an actual or synthetic component of body fluid.

A second circulation loop 203 passes diluent fluid 200 into central reservoir 230 to simulate the dilution of the therapeutic agent in a body fluid by the washing actions of new fluid(s). Accordingly, the dilution of fluid 232 by the new fluid, that is free of therapeutic agent(s), simulates the half-life of the therapeutic agent(s). The operation of the second pump 218 (also known as the dilution pump, or slow pump) passes diluent fluid 200 along the second loop 203 from the input reservoir 202 into the central reservoir 230, and passes fluid (also known as output fluid) from the central reservoir into output reservoir 250. Thus, since the amount of fluid entering central reservoir 230 is offset by the amount of fluid exiting the reservoir 230, the system can be maintained at an essentially constant amount. For example, dilution pump 218 pumps an amount of the diluent fluid from the input reservoir 202 into the central reservoir 230, and pumps essentially the same amount of output fluid at the same rate from the central reservoir 230 into output reservoir 250. Hence, the amount of dilution of therapeutic agent can be precisely controlled by the dilution pump 218.In some embodiments, e.g., as illustrated in FIG. 14, one or more pumps 218 can be utilized to add diluent fluid to the loop 201, and to remove output fluid from the loop. Thus, since the amount of fluid entering loop 201 is offset by the amount of fluid exiting the loop 201, the system can be maintained at an essentially constant amount. In another embodiment (not shown) separate pumps can be used to pump diluent fluid from input reservoir 200 into central reservoir 230, and output fluid from central reservoir 230 into the output reservoir 250.

In preferred embodiments of the invention, the rates for adding the input fluid and for removing the output fluid are substantially equal.

In some embodiments, the diluent fluid is passed into the central reservoir (and the output fluid is passed out of the central reservoir) at a rate of about 2 ml/min or less, e.g., in the range of about 0.01 to about 1 ml/min, or at a rate of about 0.1 ml/min, or about 0.2 ml/min. In some embodiments wherein the system lacks a central reservoir (e.g., as illustrated in FIG. 14), similar rates can also be utilized.

If desired for any embodiment, a single dilution pump 218 (e.g., a peristaltic pump associated with a plurality of tubes) can be utilized with a plurality of dosing systems 1000, e.g., to introduce fluid into, and withdraw fluid from, a plurality of central reservoirs and/or bioreactor loops. A variety of such pumps are suitable for carrying out the invention and are known in the art.

In an embodiment (not shown), a single pump, e.g., a pump operating different size tubing, can operate as both a fast pump and a slow pump. Thus, the single pump can pass fluid along the first circulation loop 201 at a high flow rate, and fluid along the second circulation loop 203 at a lower rate. If desired, this single pump can also be utilized with a plurality of dosing systems, as described above.

Dosing element 224 introduces the therapeutic agent 300, e.g., a liquid drug, from the agent storage area or chamber 220 into the central reservoir 230 and/or loop 201. This simulates the dosing of the therapeutic agent 300 into the circulatory system. A variety of therapeutic agents such as drugs and drug candidates are suitable for carrying out the invention. Illustrative therapeutic agents are drugs such as antiviral drugs, antibiotics, antineoplastic agents, hormones, hormone antagonists, cytokines, anti-depressives, sedatives, hypnotic agents, cardiovascular agents, hematopoietic agents, anticoagulants, anti-inflammatory agents, antimicrobial agents, anti-parasitic agents, agents affecting the nervous system, and agents affecting the immune system. As illustrated in FIG. 12, the system can include a plurality of dosing elements 224, and the system can monitor the interaction between a plurality of therapeutic agents 300.

For those embodiments including monitoring the interaction between a plurality of therapeutic agents, the half-lives can be similar for each agent, identical for each agent, or different for each agent.

Dosing element 224 is preferably a programmable dosing pump as described below. A programmable dosing pump is especially desirable for delivering very small amounts of the therapeutic agent into the central reservoir 230 (e.g., FIGS. 2, 9, 12 and 13) and/or bioreactor loop 201 (e.g., FIG. 14).

In accordance with the preferred embodiment of the invention, the therapeutic agent 300, the diluent fluid 200, and the fluid exiting the bioreactor loop 201 are passed into central reservoir 230 through mixing arrangement 400, that has outlet openings or ports leading to the central reservoir that are cooperatively arranged to allow fluid from the bioreactor loop to wash or pull fluid from the therapeutic agent port and from the diluent fluid port. This washing or pulling of fluid from the therapeutic agent port and the diluent fluid port by the fluid from the bioreactor loop port provides efficient mixing, without requiring, for example, a magnetic stirrer in the central reservoir. Moreover, the mixing arrangement according to the invention provides consistent and continuous flow, rather than stepwise additions of therapeutic agent resulting from large drops.

This is in contrast with conventional systems that deliver drugs through tubing, since the surface tension typically causes an amount of the drug to remain at the end of the tube. Each drug "drop" will only fall out when it gets large enough to fall. The drug that remains at the end of the tube is considered by the system to have been dosed, but is not actually added to the simulated body fluid. Hence, this residual drug represents an error. Therefore, the dosing is uncertain based on the surface tension of the material. Rather than providing even dosing, therefore, the conventional system provides only batch dosing: with the batch being the size of a drop. This problem is compounded when utilizing a small volume of drug at a high concentration, since the drop left from the previous dosing may account for a large portion of the dose.

A similar problem occurs elsewhere in these conventional systems, e.g., with respect to adding diluent fluid, since each diluent "drop" will only fall out when it gets large enough to fall. The drop that remains at the end of the tube is considered by the system to have been added, but is not actually added to the simulated body fluid.

In accordance with the present invention, the high flow through the bioreactor 270 obviates these problems, particularly for those embodiments that also include high flow through mixing arrangement 400. Thus, using the illustrated embodiment in FIG. 3 for reference, the mixing arrangement 400 has outlet openings or ports leading to the central reservoir that are cooperatively arranged to allow fluid from the bioreactor loop port to wash or pull liquid from the therapeutic agent port and from the diluent fluid port. The therapeutic agent and diluent fluid ports are spaced across from one another, with the bioreactor loop port positioned near the therapeutic agent and diluent fluid ports. In one preferred embodiment, the therapeutic agent and diluent fluid ports extend axially into the reservoir, more preferably extending further into the central reservoir than the bioreactor loop port, so that fluid from the bioreactor loop port pours onto at least one of the other ports, more preferably onto both the therapeutic agent and the diluent fluid ports.

Figure 3:
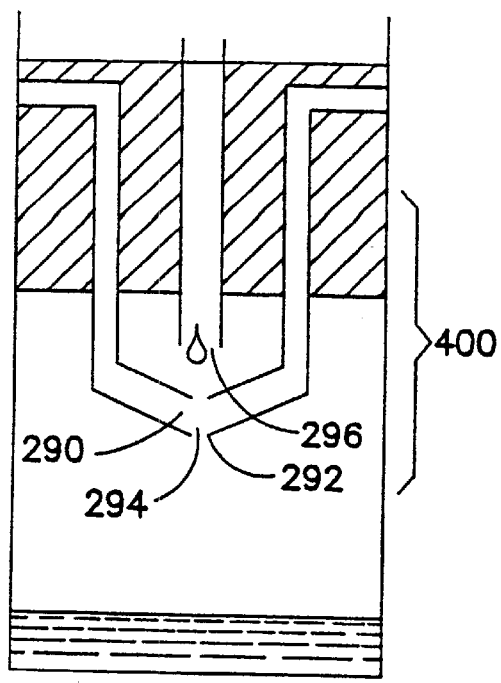
FIG. 3 shows a side view of an embodiment of a mixing arrangement according to the invention.

In the embodiments illustrated in FIGS. 2 and 3, the supply tube 204 from the input reservoir 202 leads to port or opening 290 (also known as diluent loop port 290), and the dosing tube 226 from the dosing element 224 leads to port or opening 292 (also known as therapeutic agent port 292), and these ports 290 and 292 come together at about the same area, separated by space 294. The output tube 276 from the bioreactor circulation loop 201 leads to port or opening 296 (also known as bioreactor loop port 296), and the fluid passing from port 296 washes or exhausts into space 294. Space 294 is preferably smaller than the inner diameter of the port 296 so that the outflow pours or washes over the ends of tubes 204 and 226 (ports 290 and 292). The flow of fluid from the bioreactor loop is washed or poured directly onto the ends of the two tubes 204 and 226. The high flow rate used according to this technique produces an output flow which washes out both the therapeutic agent (e.g., the drug) that remains on the end of tube 226 and the diluent fluid that remains on the end of tube 204 from the input reservoir. The high flow of fluid is continually flowing over these tube ends causing the surface-tension caused drops to continuously be diluted, removed and reformed. Among other things, the output fluid flow splashes into the interior surface of the ports 290 and 292. This operation provides a better continuum and continuous flow of therapeutic agent (s) because it does not require waiting for the drop to fall. The dispersed agent(s) and diluent fluid are essentially immediately washed out of the ports 290 and 292.

Another advantage of utilizing a mixing arrangement in accordance with the invention, preferably while utilizing a high flow rate and a low volume, is that it provides efficient mixing, without a magnetic stirrer. This is in contrast with conventional systems, that utilize a low flow rate, a larger volume, and a magnetic stirrer. Of course, in some embodiments, e.g., as illustrated in FIG. 14, that may lack a mixing arrangement 400, the high flow and low volume also provides for efficient mixing, without a magnetic stirrer. In a variation of the embodiment illustrated in FIG. 14, a therapeutic agent can be added at the input reservoir (e.g., to provide for continuous injection), and the high flow provides efficient mixing without a magnetic stirrer. In some embodiments lacking a mixing arrangement 400, the system provides a mixing area, e.g., the therapeutic agent can be added to the bioreactor loop 201 via, for example, an injection port, and the therapeutic agent mixes with the simulated body fluid.

In some embodiments, e.g., as illustrated in FIG. 9, the system includes a plurality of mixing arrangements (400, 401), each arrangement coupled to a separate reservoir, wherein each arrangement includes a plurality of ports. As described above, the ports are cooperatively arranged to allow fluid passing from one port to wash or pull liquid from the other ports in the arrangement.

Another desirable advantage provided by the combination of a mixing arrangement with a high flow rate that it provides a continuous exchange of air inside the central reservoir and facilitates gas exchange. Thus, embodiments of the invention provide efficient gas exchange without oxygenation coils, i.e., coils with thin walls and high surface areas to oxygenate material. Previous systems of this type used oxygenation coils, which took up a lot of room and required special areas to be dedicated for them.

Additionally, or alternatively, efficient gas exchange can be accomplished in accordance with the present invention in a reduced sized system, e.g., by utilizing a $CO_2$ and/or $O_2$ injection system, thus avoiding the need for a bulky incubator. Typically, the $CO_2$ injection system provides a $CO_2$ concentration in the range of from about 2.5 to about 10%, e.g., about 5%.

Since incubators, magnetic stirrers and/or oxygenation coils can be eliminated, the present invention is especially suitable for miniaturization. Some embodiments, e.g., using a heating element to control the temperature of the fluid in the system, rather than placing the system in an incubator, are also especially suitable for miniaturization. In one embodiment, the system can be sufficiently miniaturized to fit on a desktop.

As noted earlier, the present invention utilizes at least one fast pump 260 that operates at a high flow rate, e.g., about 15 ml/min or more, and typically utilizes a small total amount of fluid, e.g., about 50 ml or less, in the central reservoir 230 and the bioreactor loop 201, using the embodiment illustrated in FIG. 2 for reference. In a more preferred embodiment, the total amount is about 35 ml, and the flow rate is about 20 ml/min or more, e.g., about 50 ml/min or more, or about 70 ml/min or more. In one embodiment, the flow rate is about 200 ml/min. This goes against the established teaching in the art that utilizes a much lower trickle flow rate, e.g., about 4 ml/min or less, as well as utilizing a larger amount of fluid, e.g., about 100 ml. Illustratively, the preferred embodiments of the invention utilize a flow rate that is about 4 times greater, and about ⅓ of the volume, of conventional systems.

As noted above, the high rate of fluid turnover of the present invention assists in providing effective mixing, and thus allows the elimination of magnetic stirrers and/or oxygenating coils, which in turn allows miniaturizng the system.

Additionally, utilizing a high flow rate, preferably while, for example, maintaining back pressure in the bioreactor 270, facilitates therapeutic agent (drug) interaction with the contents of the bioreactor. While the mechanism is not well understood, the formation of the back pressure in the bioreactor apparently forces the therapeutic agent to more evenly disperse over the large internal surface area of the cartridge in the bioreactor. Without being held to a particular theory, it is believed that this back pressure forces the fluid 232 into the simulated intra-capiflary spaces in the cartridge. This results in better contact between the drug and the cells, and hence better simulation of their reactions.

In one embodiment, different diameters are used for the input and the output of the bioreactor 270 to provide (in combination with a high flow rate) back pressure in the bioreactor. For example, the diameter of the bioreactor input 278 can be larger than the diameter of the bioreactor output 280. Illustratively, input 278 can be a ⅛-inch diameter tube. Output 280, in contrast, can be a tube which has less than half the diameter of the input tube. For example, the output tube 280 can be ¹⁄₁₆th to ¹⁄₆₄th of an inch. Of course, other techniques for producing a back pressure include, for example, placing a restriction in the tube 276. Alternatively, or additionally, a flow rate controller can be utilized upstream and/or downstream of the cartridge. For example, a flow rate controller can be used to vary the lumen volume of the input of the cartridge as compared to the output.

In some embodiments, a system according to the invention can be used to model simulate absorption of a drug from the gastrointestinal tract. For example, as illustrated in FIG. 9, the dosing reservoir 350 simulates the gastrointestinal tract. Over time, drug in this reservoir will be absorbed. As time passes, less and less drug will be in the gastrointestinal tract. In accordance with the invention, this can be simulated by diluting drug in the dosing reservoir 350 by adding fluid 303 that lacks the drug. As illustrated in FIG. 9, this additional fluid 303, that lacks the drug, is passed (using a slow pump) from the dose diluent input reservoir 302. A separate mixing arrangement is coupled to the central reservoir and the dosing reservoir (elements 400 and 401 respectively), and the ports are cooperatively arranged as described with respect to FIGS. 2 and 3. Thus, fluid passing from one port washes fluid from the other ports in each reservoir. The use of a dose diluent output reservoir 402 allows the amount of fluid added to dosing reservoir 350 from dose diluent input reservoir 302 to be essentially offset by passing fluid from reservoir 350 into the output reservoir 402.

Using FIG. 9 for reference, in some embodiments the slow pumps 218 operate a different rates and/or for different periods of time. For example, slow pump 218 associated with second loop 203 can operate continuously at a rate to represent the half-life of the therapeutic agent. Each of the other slow pumps 218, i.e., slow pump 218 interposed between dose diluent reservoir 302 and dosing reservoir 350, and slow pump 218 interposed between dosing reservoir 350 and central reservoir 230, can be operated at different rates for different periods of time to reflect absorption and dosing.

In preferred embodiments, e.g., as illustrated in FIGS. 2, 9, and 12–14, the supply of the therapeutic agent 300 (such as a drug or drug candidate) is controlled by a dosing element 224 such as a dosing pump, more preferably, a programmable dosing pump. These dosing pumps are well known and are commercially available, and are used, for example, for administering drugs to patients. The dosing element provides for adjusting the drug storage position 222. The output of dosing pump 224 is a tube 226 (e.g., a silicon tube) which leads to central reservoir 230, or dosing reservoir 350 (FIG. 9). Alternatively, as illustrated in FIG. 14, the output of dosing pump 224 leads to loop 201.

Another important feature of the present invention is its capability to change the type of therapeutic agent and type of dosage and dosing system that is used. Therapeutic agents such as drugs are absorbed in different ways, depending on the kind of administration. When drugs are dosed intravenously, they are typically immediately adsorbed into the human blood system. In contrast, drugs which are dosed orally often have a lag time until absorption, and are then absorbed slowly. Other absorption characteristics may depend on the drug absorption mechanism. Different characteristics of the way drugs are absorbed are well known.

Figure 7:
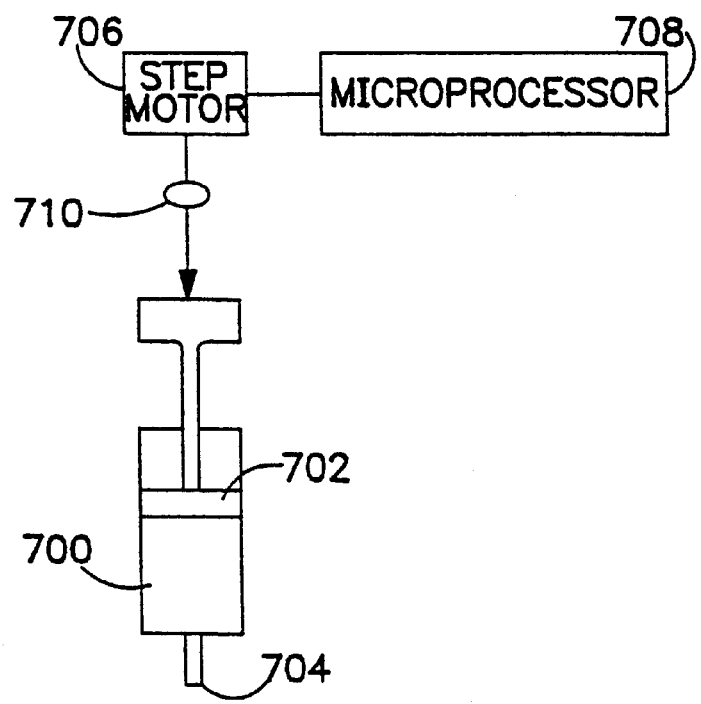
FIG. 7 illustrates a programmable dosing pump.

The dosing pump of the present invention is preferably programmable to simulate these functions and many others. Additionally, the pump should be programmable to provide ascending and/or descending therapeutic agent concentrations. Specifically, the dosing pump can be programmed to simulate both intravenous and oral administration characteristics. FIG. 7 illustrates an exemplary dosing pump and its controller. As conventional in the art, the dosing element itself is typically a syringe with a pressing element. Chamber 700 includes the therapeutic agent, e.g., a drug, therein. The chamber 700 is bounded by a moveable plunger 702. Plunger 702 can be moved up and down relative to the holding chamber 700. When plunger 702 is pressed down, it reduces the chamber size and forces some of the drug out delivery tube 704.

Typically, the system is controlled by a stepping motor 706 which is controlled by a programmed microprocessor 708. Stepper motor 706 produces a controlled and highly precise amount of movement per pulse from the microprocessor. For example, stepper motor might rotate 2° per pulse. The output shaft of the stepper motor 706 is connected to a threaded screw 710 that moves downward by a predetermined amount per screw revolution. For example, a screw with 32 threads per mm moves downward 1/32 mm per revolution:

$$\frac{(2°/\text{pulse}) \cdot (1/32\,\text{mm/rev})}{(360°/\text{rev})} = 1/32 \cdot 180 = 1.73 \times 10^{-4}\,\text{mm/pulse}$$

More generally the doser moves by $$\frac{S}{T}\,\text{mm/pulse} \qquad (1)$$

where T is the number of threads per mm and S is the percentage of revolution per pulse=degrees per pulse/360.

If the tube is of radius r, then each pulse delivers $$\frac{S\pi r^2}{T}\,\text{ml}$$

of drug per pulse. In the above example, an 1/8 inch OD tube with 1/32" walls has an inner diameter of about 1/16 inch which is about 1.6 mm. Each pulse therefore delivers approximately $1.37 \times 10^{-3}$ ml or approximately 1.37 μl.

Figure 8:
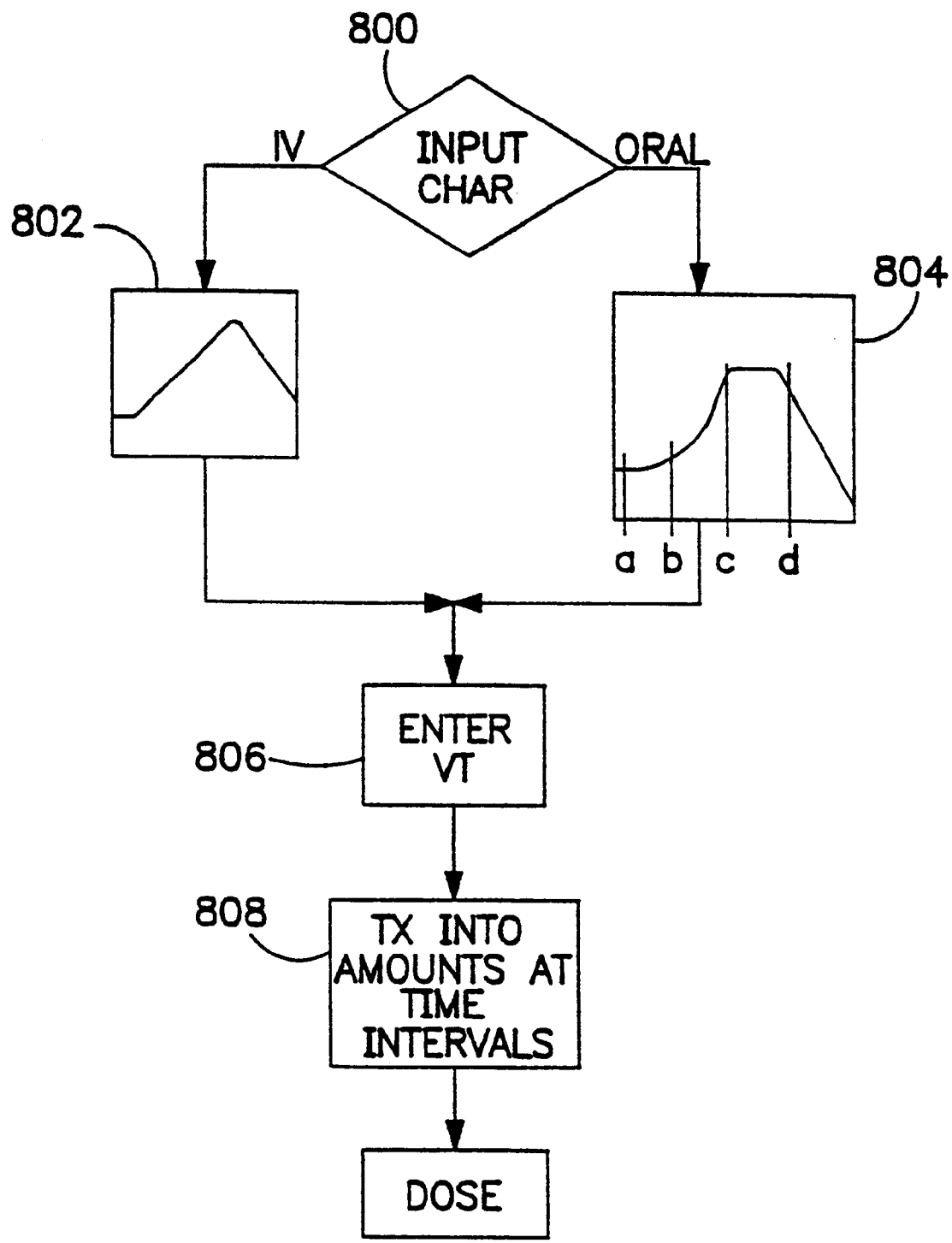
FIG. 8 shows a flow chart of operation to control a programmable dosing pump in accordance with the present invention.

The operation is controlled by microprocessor 708, which can be a personal computer, for example. Illustratively, the microprocessor is controlled according to the flow chart shown in FIG. 8. Step 800 obtains an indication of the drug dosage characteristics. The input characteristics can be an intravenous, oral, or any other prestored or user-defined characteristic. For example, the curve envelope shown in step 802 can be loaded for an intravenous (IV) administration. Alternately, the input characteristic could be oral, in which case the curve envelope shown in step 804 can be loaded. Preferably, these general curve envelopes are modelled in the form of equations or time-sensitive instructions. For example, for the model 804, the instructions might say for time a do nothing. From time a to time b, gradually increase the slope of the curve by 0.1 per second, time b to time c level off, and from time d on reduce the curve by slope 0.1. A similar characteristic or equation could be used to simulate any desired curve.

Step 806 determines the total volume of drug to be administered. This corresponds to the area under either of the curves shown in step 802 or 804. Each of the curves is stored as a unit curve, e.g., intended to be multiplied by a variable X. The total area under the curve determines this multiplicand. At step 808, the computer translates the two sets of parameters into the amount of time that should elapse between pulses—i.e., how long should there be between deliveries of 1.37 μl amounts to be dosed at separated time intervals.

For example, the system at step 804 does nothing until time a. From b through c, the system calculates the dose according to the curve, where the curve increases in slope by 0.1 every 5 minutes. Since the value of the curve if always known, the curve itself can be calculated, and how often the pump needs to be pulsed can be determined. Using the example above, the dosing system delivers about 1.37 μl per pulse. If, therefore, a dosage of 1 ml per second is needed during that time, pulses are needed every 1.37e-6/1e-3=1.37 ms. At step 810, this system is dosed by pulsing at appropriate times.

Other Components of the System

A variety of containers are suitable for use as the reservoirs, i.e., the input reservoir 202, the output reservoir 250, the central reservoir 230, the dose diluent input reservoir 302, the dose diluent output reservoir 402, and the dosing reservoir 350, and are known in the art. As will be noted in more detail below, the reservoirs 202, 230, 250, 350, 402 and 302 are typically sealed. In some embodiments, reservoirs 202, 230, 250, 350, 402 and/or 302 also include a cap such as a cover or stopper that provides an essentially air tight seal for the reservoirs and the conduits such as tubes or pipes entering the reservoirs.

A variety of caps are suitable for carrying out the invention, and are known in the art. Similarly, a variety of conduits such as tubes or pipes are suitable for providing fluid communication between the elements of the system in accordance with the invention, and are known in the art. For example, suitable tubing can have a circular cross-section or a rectangular inner diameter. Other types of tubing, e.g., including low profile shapes that self-flatten, can also be used. Tubing with rectangular inner diameters might be especially conducive to the tubing connector described herein.

In the embodiment illustrated in FIG. 2, input reservoir 202 includes a cap 208; output reservoir 250 includes a cap 251, and central reservoir 230 includes a cap 231. System 1000 also includes a supply tube 204 that has an end or port that will remain immersed in diluent fluid 200, e.g., tube 204 can extend to an area 206 close to the bottom of the reservoir into the diluent solution 200. Supply tube 204 provides fluid communication with the mixing arrangement 400 in central reservoir 230. The system also includes an output tube 210 that passes the output from central reservoir 230 into the output reservoir 250, and additional tubes as noted earlier, e.g., tubes 226, 262, 276, and 212a–c. The system can also have components such as reservoirs, caps, tubes, and vents, e.g., as illustrated in FIGS. 9, and 12–14.

Typically, reservoirs 202, 250, 230, 350, 402, and 302 are substantially airtight except for the pressure balancing tubes 212a, 212b, 212c, 212d, 212e, and 212f. Each pressure balancing tube 212a–f preferably includes an air vent with air filter 214. Using FIG. 2 for reference, ambient air pressure in the air portion 216 of the input reservoir, the air portion of output reservoir 250, and the air portion of the central reservoir are equalized by the vents. As the liquid is passed out of input reservoir 202, air takes its place through a pressure balancing tube 212a, and as liquid is passed out of central reservoir 230, air takes its place through a pressure balancing tube 212c. As liquid is passed into output reservoir 250, air is displaced from the reservoir to the atmosphere through pressure balancing tube 212b.

The Tubing Assembly

One disadvantage of conventional systems using cartridges in parallel is the so-called "spaghetti" phenomenon, wherein confusion among the various tubes may lead to failures when attempting to use the cartridges. Since each cartridge or cell might include as many as five to ten tubes, and at least two cartridges should be operated at the same time, i.e., one as a control, and at least one for testing the parameter of interest, the use of two units in parallel results in at least ten tubes that look similar and which all need to be properly located. Moreover, the tubes are flexible and hence it is very difficult to determine the place where any end is connected. Connecting any tube incorrectly, e.g., to the wrong port, could compromise the whole experiment. An advantage of embodiments of the present invention is to obviate this problem by providing a special system, i.e., tubing assembly, which keeps all of the tubes ordered relative to one another.

Figure 6:
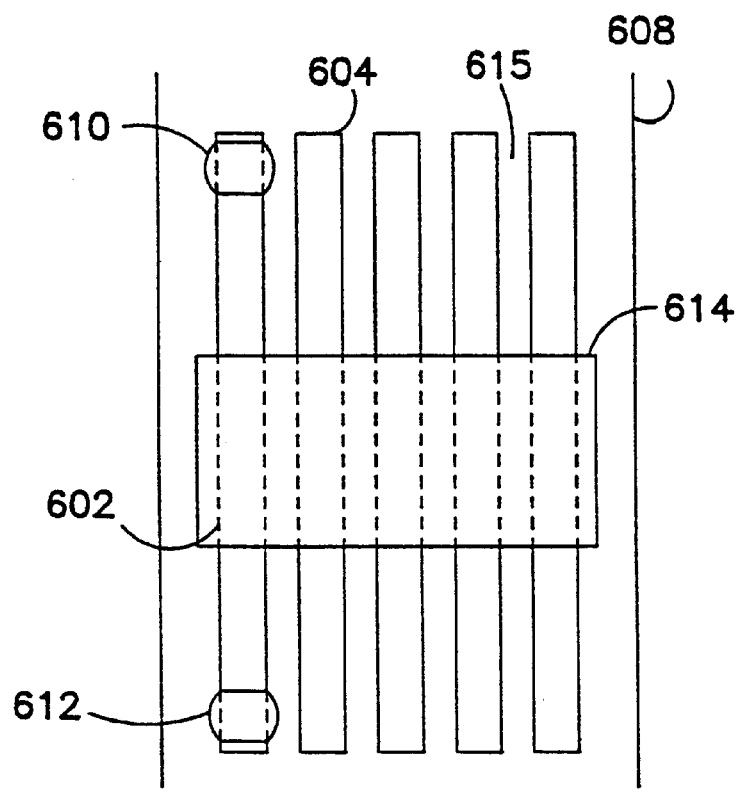
FIG. 6 shows a mold used for bundling tubing according to the present invention.

One example of a tubing assembly according to the invention is shown in FIG. 6. Eight or ten lengths 602, 604 of tubing, e.g., ⅛ inch silicon tubing, are laid side-by-side in a mold 608. A variety of molds are suitable for carrying out the invention, e.g., a formal mold, or sheet(s) of aluminum foil. In this ordered arrangement, it is easy to ascertain which tube is which. Color coded beads 610, 612 are preferably placed at the ends of the tubes. Therefore, for example, tube 602 includes beads 610 and 612, both of which are red. Tube 604 includes other colored beads such as blue. The color-coded beads allow identifying each tube of the bundle relative to others. An alternative to the color coding, however, is that each tube of the bundle is identified simply by its position within the bundle.

Of course it should be understood that this tubing connector need only identify which tube is which within the bundle. While the bundle shown herein is a flat bundle which enables distinguishing between tubes by position in the bundle, it could alternately be a tubular shaped bundle, which uses the color codes, by some other marking on the tube, or one which allows determining by some aspect of the position of the tube within the sphere. Other shapes include, for example, a spiral bundle.

The mold 608 is then conformed to the tubes in order to squeeze them together and maintain them close to one another. Each of the tubing pieces 602/604 are still essentially straight. Preferably, a binding agent, e.g., an adhesive such as clear silicon, is applied to the top and side surfaces of the tubes. This can be done, for example, by applying silicon from a caulking gun. If desired, a spreader such as a spatula can be used to more evenly coat the top surfaces of the material (e.g., area 614), and to force the adhesive into the areas 616 between each two adjacent tubes. The ends of the tubing, e.g., several inches at each end, are left uncoated to allow some room to connect the tubes.

Preferably, after the adhesive has dried, e.g., for about 24 to about 48 hours, the assembly is removed from the mold, and turned over so that the other side can be coated in a similar way. However, the assembly can be used according to the invention with only one side treated as described above.

This system forms bundles of tubes, all kept together relative to one another as compartmentalized elements. Since the tubes all stay together relative to one another, this operation avoids the spaghetti effect. The tubing system used in the systems of FIG. 1 are preferably tubing assemblies as shown in FIG. 6. For example, each input and output reservoir may be arranged in a bank, and the bank is connected to elements of these tubing assemblies.

While silicon has been described herein as the adhesive material for holding together this tubing, other materials and techniques of holding the tubes relative to one another could also be used. Importantly, some surface must be provided to hold the tubes relative to one another to avoid tangling and confusion of the tubes.

EXAMPLES

Example 1

This Example illustrates simulating different drug half-lives in accordance with the invention.

A system is generally arranged as illustrated in FIG. 2. The reservoirs are stoppered transparent beakers. The volume of distribution (VD) which is total amount of fluid in the loop 201 and the central reservoir 230 is 50 ml. The fast pump is operated at a flow rate of 35 ml/min. The dilution pump 218 is operated to provide a specific clear rate (flow rate) for a specified amount of time, to establish a specific half-life ($t_{1/2}$). The pump setting (% Maximum) is adjusted over time to provide the desired clear rate over time. The pump is initially set at 56.3 to provide a clearance rate of 34.65, and a half-life of 1 hour. The results are provided in Table I.

TABLE I

SIMULATIONS OF DIFFERENT DRUG HALF-LIFE IN THE DOSING SYSTEM

| t1/2 (h) | Calculated clearance (ml/hr) | PUMP SETTING % Maximum |
|---|---|---|
| 1 | 34.650 | 56.3 |
| 2 | 17.325 | 28.0 |
| 3 | 11.550 | 18.6 |
| 4 | 8.663 | 13.9 |
| 5 | 6.930 | 11.1 |
| 6 | 5.775 | 9.2 |
| 7 | 4.950 | 7.9 |
| 8 | 4.331 | 6.9 |
| 9 | 3.850 | 6.1 |
| 10 | 3.465 | 5.5 |
| 11 | 3.150 | 4.9 |
| 12 | 2.888 | 4.5 |
| 13 | 2.665 | 4.2 |
| 14 | 2.475 | 3.8 |
| 15 | 2.310 | 3.6 |
| 16 | 2.166 | 3.3 |
| 17 | 2.038 | 3.1 |
| 18 | 1.925 | 3.0 |
| 19 | 1.824 | 2.8 |
| 20 | 1.733 | 2.6 |
| 21 | 1.650 | 2.5 |
| 22 | 1.575 | 2.4 |
| 23 | 1.507 | 2.3 |
| 24 | 1.444 | 2.2 |

Example 2

A system is generally arranged as illustrated in FIGS. 1 and 2, utilizing 5 dosing systems operating in parallel, wherein one system is a control.

The bioreactor includes a cartridge of polypropylene capillaries that is commercially available from Unisyn Technologies, Inc. (Hopkinton, Mass.). The cells in the bioreactor are a human T-lymphoblastic cell line CEM, infected with HIV. The volume of distribution (VD), which is total amount of fluid in the loop 201 and the central reservoir 230, is 50 ml. The fast and slow pumps are Ismatic Peristaltic Pumps commercially available from Cole-Parmer (Niles, Ill.). The dosing element is a programmable dosing pump commercially available from Medex, Inc. (Deluth, Ga.).

The fast pump is operated at a flow rate of 35 ml/min. The dilution pump 218 is operated at a flow rate of 0.5 ml/min.

The drug Zidovudine (ZDV) is infused at four different dosing regimens for a dosing period of 24 hours, i.e., 0.1 µg/ml, continuously at 0.37 µM; 100 µg every 8 hours; 150 µg every 12 hours; and 300 µg at 24 hours. The control is operated without dosing ZDV.

Samples are removed through sampling port 272. Extracellular concentrations are determined from the fluid, and intracellular concentrations are determined after harvesting and treating the cells to extract the contents.

Drug concentration time curves allow the determination of $C_{max}$, $C_{min}$ and AUC.

Figure 10:
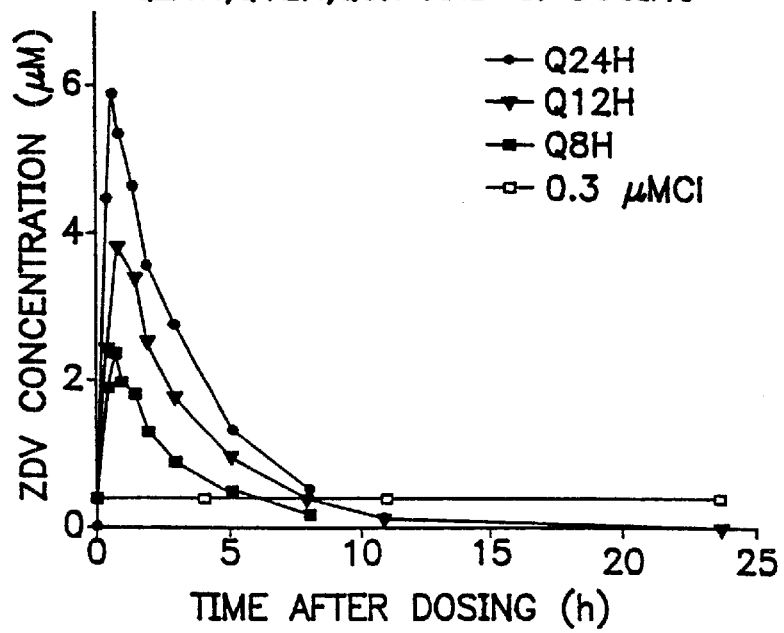
FIG. 10 shows the pharmacokinetic curves of a drug infused at different dosing regimens in accordance with the invention. The curves illustrate the extracellular drug concentration.

FIG. 10 shows the pharmacokinetic curve illustrating the drug concentration outside the cells (extracellular concentration).

Figure 11A:
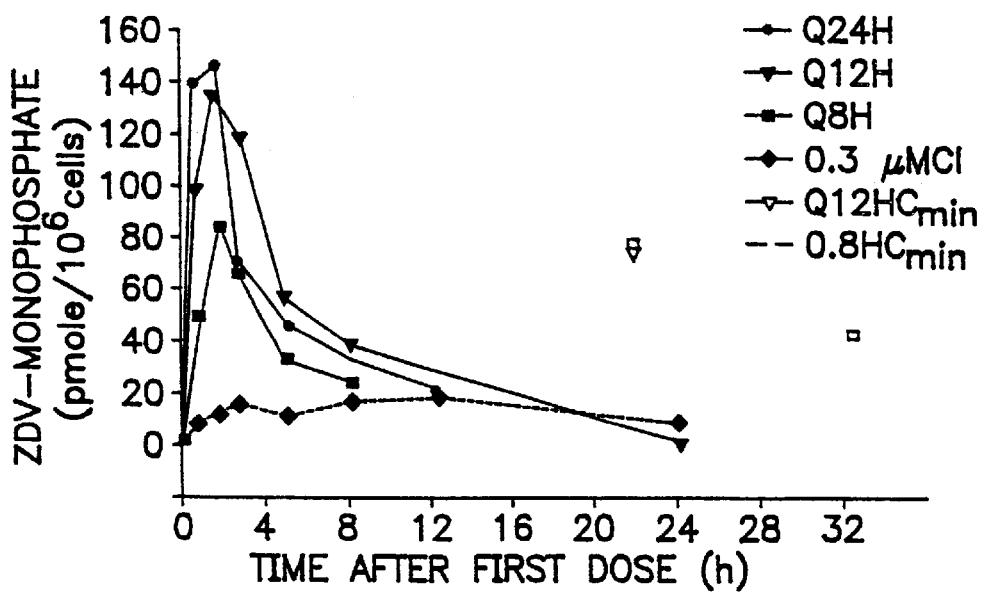
FIG. 11 (a, b, and c) shows the pharmacokinetic curves for three measured metabolites of a drug ineused at different dosing regimens in accordance with the invention. The curves illustrate the intracellular drug concentrations of the metabolites.
Figure 11B:
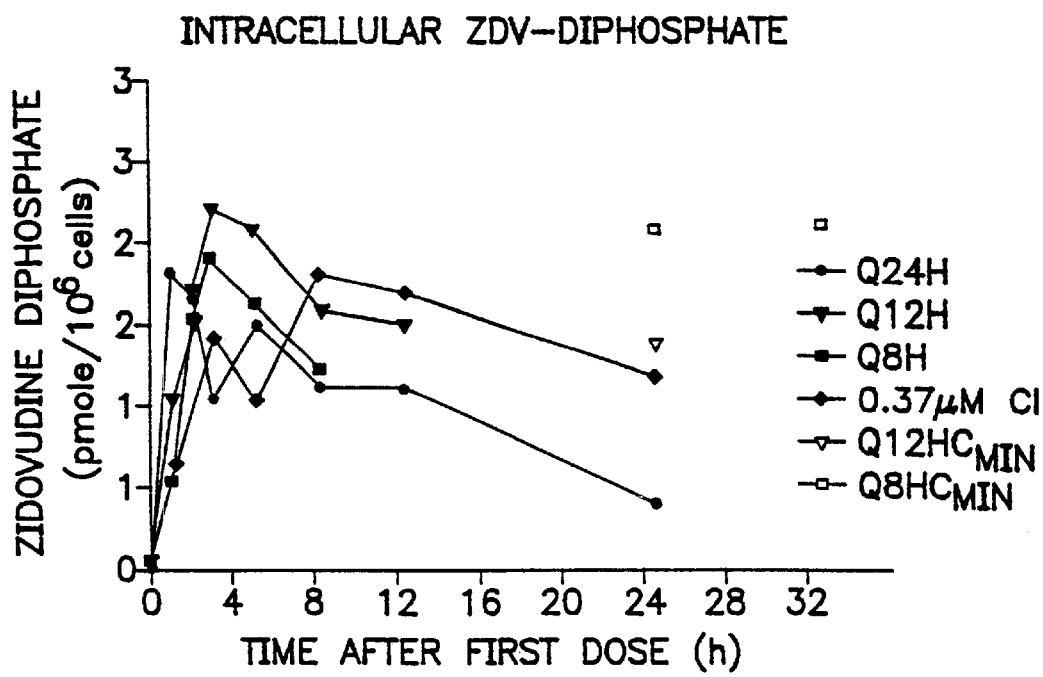
Figure 11C:
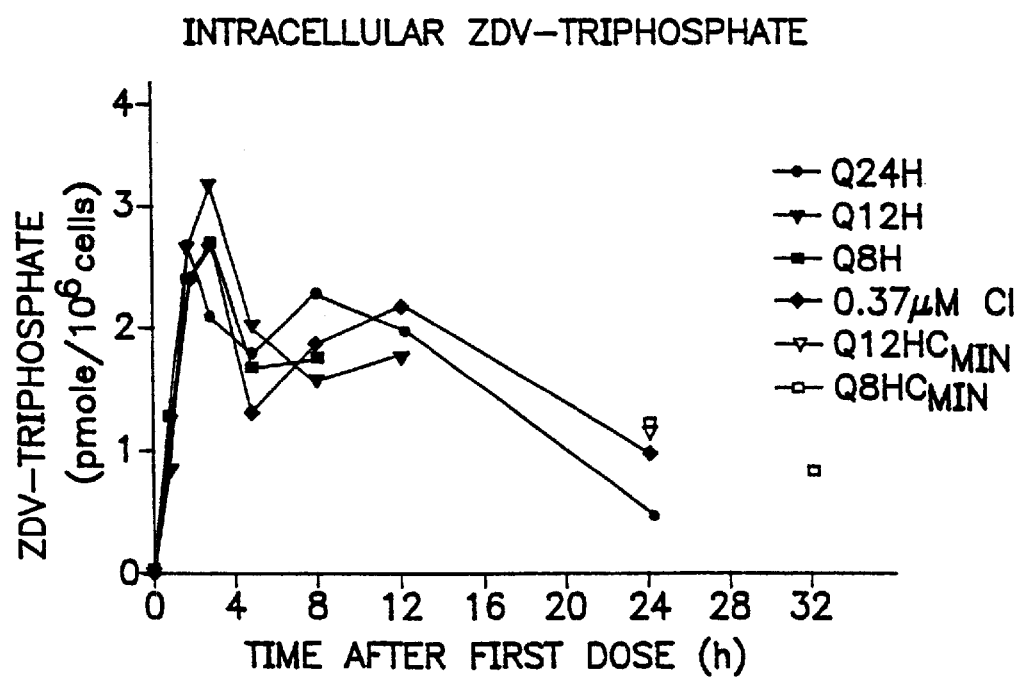

FIG. 11 (a, b, and c) shows the intracellular pharmacokinetic profiles for three ZDV metabolites, i.e., ZDV-monophosphate, ZDV-diphosphate, and ZDV-triphosphate. The results of this experiment shows that dosing ZDV in these four different ways resulted in different profiles for the intracellular ZDV monophosphate concentration (FIG. 11 a). However, intracellular diphosphate and intracellular triphosphate have similar profiles (FIGS. 11 b and c). Thus, the AUCs are similar for the intracellular ZDV-diphosphate and intracellular ZDV-triphosphate.

It appears from these data that extracellular concentration of ZDV correlates relatively well with the intracellular concentration of ZDV-monophosphate. However, all four dosing regiments, which achieve significantly different pharmacokinetic profiles, appear to result in the same amount of ZDV-triphosphate, which is the active metabolite. It is known that ZDV-monophosphate converts to ZDV-diphosphate and ZDV-diphosphate converts to ZDV-triphosphate inside the cell. ZDV-triphosphate is a metabolite that inhibits HIV reverse transcriptase, which results in the inhibition of HIV replication. The data suggest that the rate limiting step is the conversion of ZDV-monophosphate to ZDV-iphosphate. Therefore, increasing the dose of ZDV results in a relative increase in intracellular ZDV-monophosphate concentration, but that does not result in an increase in the concentration of ZDV-diphosphate or ZDV-triphosphate.

The data above suggest that giving more ZDV to humans does not always correlate with a parallel increase in antiviral activity. The results from these experiments suggest that dosing ZDV to patients may need to be modified to allow maximum formation of ZDV-triphosphate that can be maintained through the dosing intervals at concentrations that are inhibitory to viral replication.

The data also suggest that increasing the plasma concentration of ZDV, which is equivalent to the concentrations of ZDV that was measured in the PK/PD system in this Example, does not always mean that a higher dose would be beneficial. Thus, the PK/PD system of the present invention allows one to optimize dosing of a therapeutic agent, e.g., as drug such as ZDV, to humans.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A device comprising:
    a reservoir;
    a mixing arrangement;
    the reservoir being coupled to the mixing arrangement;
    the mixing arrangement including a bioreactor loop conduit including a bioreactor loop port, a diluent loop conduit including a diluent loop port, and a therapeutic agent conduit including a therapeutic agent port; and
    the bioreactor loop port being positioned near the diluent loop port and the therapeutic agent port, wherein the diluent loop conduit, the therapeutic agent conduit, and the bioreactor loop conduit each extend into the reservoir.

2. The device of claim 1 wherein the diluent loop port is spaced across from the therapeutic agent port.

3. The device of claim 1 wherein the bioreactor loop port is positioned to allow fluid from the bioreactor loop port to pass from the port onto the diluent loop port or the therapeutic agent port.

4. The device of claim 1 having a distance between the diluent loop port and the therapeutic agent port that is less than the inner diameter of the bioreactor loop port.

5. The device of claim 1 further comprising a dosing element in fluid communication with the therapeutic agent conduit and the therapeutic agent port, and wherein the dosing element comprises a programmable pump.

6. The device of claim 1 wherein the diluent loop conduit and the therapeutic agent conduit each extends axially into the reservoir.

7. A device comprising:

a reservoir;

a mixing arrangement;

the reservoir being coupled to the mixing arrangement;

the mixing arrangement including a bioreactor loop port, a diluent loop port, and a therapeutic agent port;

wherein the bioreactor loop port is positioned near the diluent loop port and the therapeutic agent port, and the bioreactor loop port is positioned to allow fluid from the bioreactor loop port to pass from the port onto the diluent loop port or the therapeutic agent port.

8. A device comprising:

a reservoir;

a mixing arrangement;

the reservoir being coupled to the mixing arrangement;

the mixing arrangement including a bioreactor loop port, a diluent loop port, and a therapeutic agent port;

the bioreactor loop port being positioned near the diluent loop port and the therapeutic agent port; and, a dosing element in fluid communication with the therapeutic agent conduit and the therapeutic agent port, wherein the dosing element comprises a programmable pump.

* * * * *